US008618250B2

(12) United States Patent
Russell et al.

(10) Patent No.: US 8,618,250 B2
(45) Date of Patent: Dec. 31, 2013

(54) DESIGNER COLLAGENS AND USE THEREOF

(75) Inventors: Brooke H. Russell, Pearland, TX (US); Magnus Hook, Houston, TX (US); Mariah S. Hahn, College Station, TX (US); Elizabeth M. Cosgriff-Hernandez, College Station, TX (US); Neungseon Seo, Carmel, IN (US); Marvin Xuejun Xu, Missouri City, TX (US)

(73) Assignee: The Texas A&M University System, College Station, TX (US)

( * ) Notice: Subject to any disclaimer, the term of this patent is extended or adjusted under 35 U.S.C. 154(b) by 146 days.

(21) Appl. No.: 12/804,306

(22) Filed: Jul. 19, 2010
(Under 37 CFR 1.47)

(65) Prior Publication Data

US 2011/0288274 A1    Nov. 24, 2011

Related U.S. Application Data

(60) Provisional application No. 61/335,432, filed on Jan. 7, 2010, provisional application No. 61/271,218, filed on Jul. 17, 2009.

(51) Int. Cl.
*C07K 14/00*    (2006.01)

(52) U.S. Cl.
USPC ............................................. 530/350

(58) Field of Classification Search
USPC ............................................. 530/350
See application file for complete search history.

(56) References Cited

U.S. PATENT DOCUMENTS

| | | | | |
|---|---|---|---|---|
| 6,150,081 | A * | 11/2000 | Van Heerde et al. | 430/569 |
| 6,171,827 | B1 * | 1/2001 | Bulleid et al. | 435/69.7 |
| 7,504,490 | B1 * | 3/2009 | Weinstock et al. | 536/23.1 |
| 7,745,391 | B2 * | 6/2010 | Mintz et al. | 514/19.3 |
| 2006/0035336 | A1 | 2/2006 | Hook et al. | |
| 2007/0099244 | A1 | 5/2007 | Xu et al. | |

OTHER PUBLICATIONS

Extended European Search Report for 108001769, dated Apr. 18, 2012, 6 pages.
Han, Runlin, et al., "Assessment of Prokaryotic Collagen-Like Sequences Derived from Streptococcal Scl1 and Scl2 Proteins as a Source of Recombinant GXY Polymers," Applies Genetics and Molecular Biotechnology, (2006), 72:109-115.
Seo, Neungseon, et al., "An Engineered α1 Integrin-Binding Collagenous Sequence," The Journal of Biological Chemistry, Oct. 1, 2010, vol. 285, No. 40, pp. 31046-31054.
Caswell, Clayton C., et al., "Identification of the First Prokaryotic Collagen Sequence Motif that Mediates Binding to Human Collagen Receptors, Integrins α2β1 and α11β1," The Journal of Biological Chemistry, Dec. 26, 2008, vol. 283, No. 52, pp. 36168-36175.
Hoe, Nancy P., et al., "Characterization of the Immune Response to Collagen-Like Proteins Scl1 and Scl2 of Serotype M1 and M28 Group a *Streptococcus*," FEMS Microbiol Lett, (2007), pp. 142-149.
Humtsoe, Joseph O., et al., "A Streptococcal Collagin-Like Protein Interacts with the α2β1 Integrin and Induces Intracellular Signaling," the Journal of Biological Chemistry, (2005), vol. 280, No. 14, pp. 13848-13857.
Kim, Jiyeun Kate, et al., "A Novel Binding Site in Collagen Type III for Integrins α1β1 and α2β1," The Journal of Biological Chemistry, Sep. 16, 2005, vol. 280, No. 37, pp. 32512-32520.
Mohs, Angela, et al., "Mechanism of Stabilization of a Bacterial Collagen Triple Helix in the Absence of Hydroxyproline," The Journal of Biological Chemistry, Oct. 12, 2007, vol. 282, No. 41, pp. 29757-29765.
Raynal, Nicolas, et al., "Use of Synthetic Peptides to Locate Novel Integrin α2β1-Binding Motifs in Human Collagen III," The Journal of Biological Chemistry, Feb. 17, 2006, vol. 281, No. 7, pp. 3821-3831.
Sweeney, Shawn M., et al., "Angiogenesis in Collagen I Requires α2β1 Ligation of a GFP*GER Sequence and Possibly p. 38 MAPK Activation and Focal Adhesion Disassembly," The Journal of Biological Chemistry, Aug. 15, 2003, vol. 278, No. 33, pp. 30516-30524.
Xu, Yi, et al., "Multiple Binding Sites in Collagen Type I for the Integrins α1β1, and α2β1," The Journal of Biological Chemistry, Dec. 15, 2000, vol. 275, No. 50, pp. 38981-38989.
Xu, Yi, et al., "Streptococcal Scl1 and Scl2 Proteins form Collagen-Like Triple Helices," The Journal of Biological Chemistry, Jul. 26, 2002, vol. 277, No. 30, pp. 27312-27318.
Yoshizumi, Ayumi, et al., "Self-Association of *Streptococcus* Pyogenes Collagen-Like Constructs into Higher Order Structures," Protein Science, (2009), vol. 18:1241-1251.
International Search Report for PCT/US2010/002029, dated Apr. 26, 2011, 6 pages.
International Preliminary Report on Patentability for PCT/US2010/002029 dated Jan. 17, 2012.

\* cited by examiner

*Primary Examiner* — Karen Cochrane Carlson
(74) *Attorney, Agent, or Firm* — Chainey P. Singleton; Edwin S. Flores; Chalker Flores, LLP

(57) ABSTRACT

The present invention identified a recombinant synthetic collagen containing a triple helical backbone protein produced in a prokaryotic expression system where the protein contains at least one 'inserted' biologically active sequence(s).

18 Claims, 25 Drawing Sheets

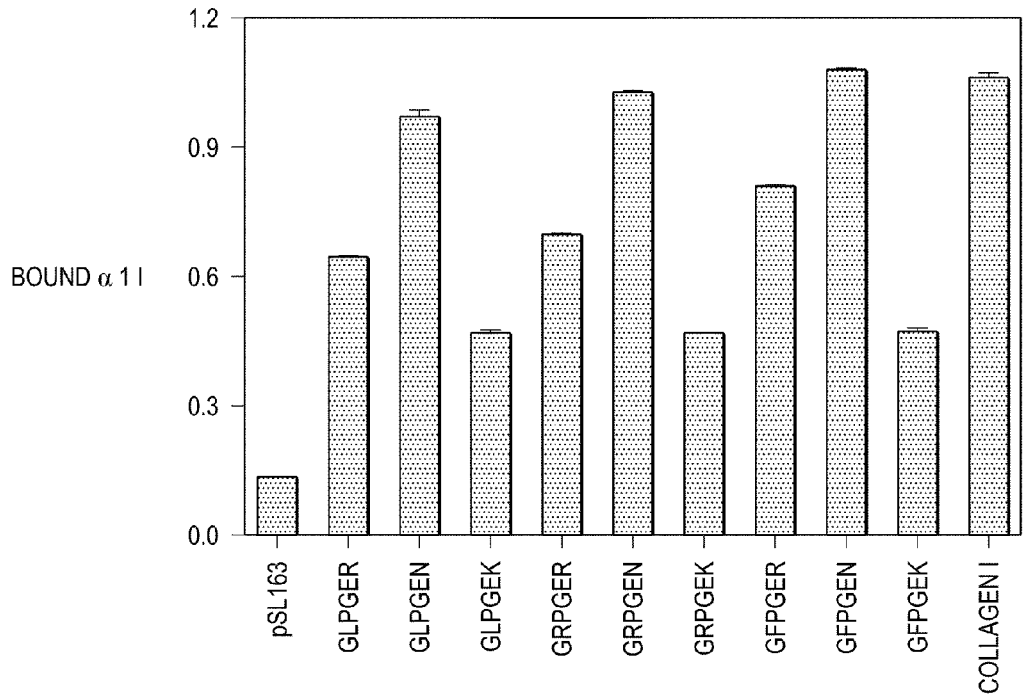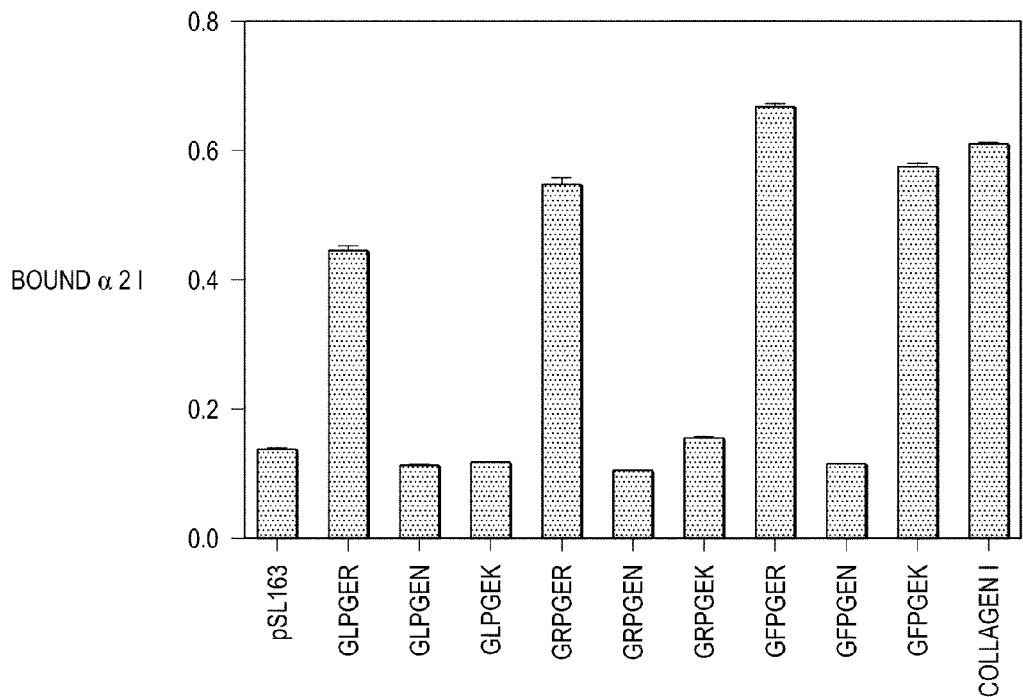

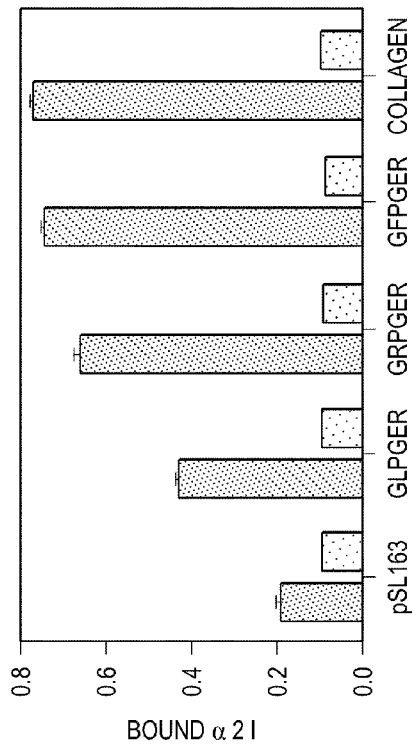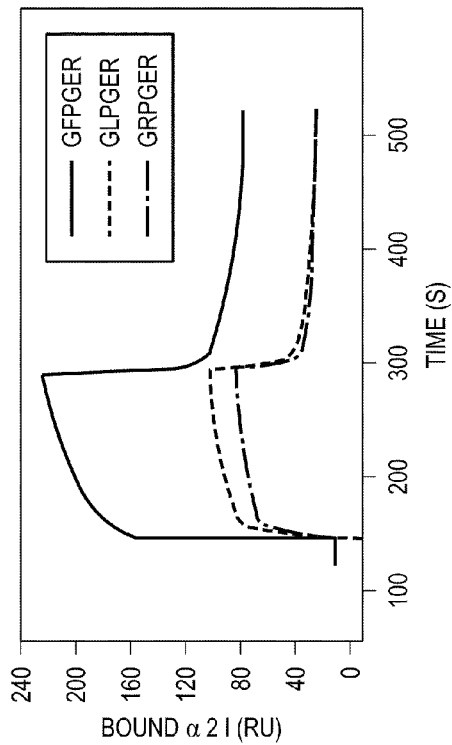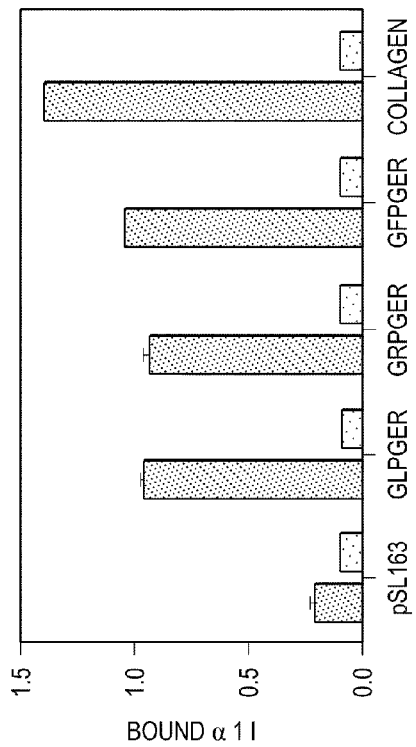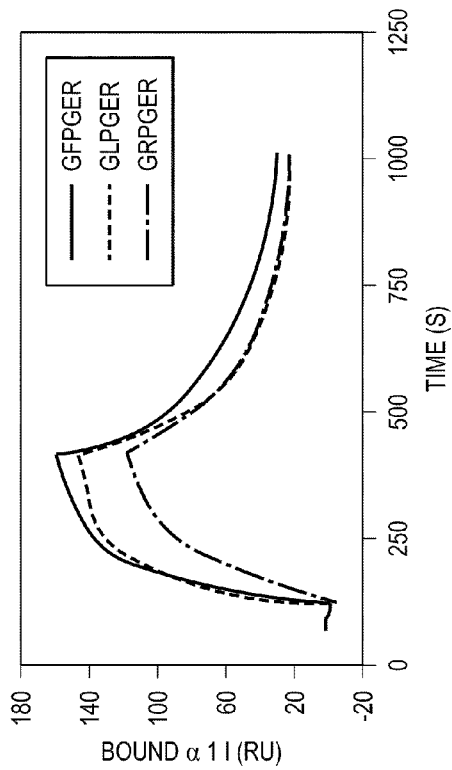

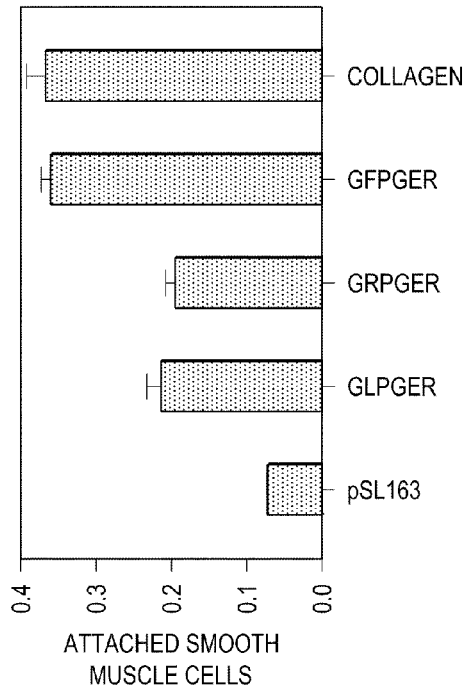
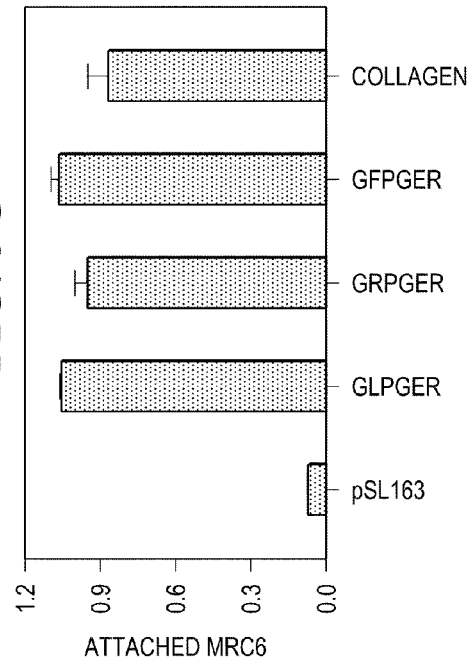
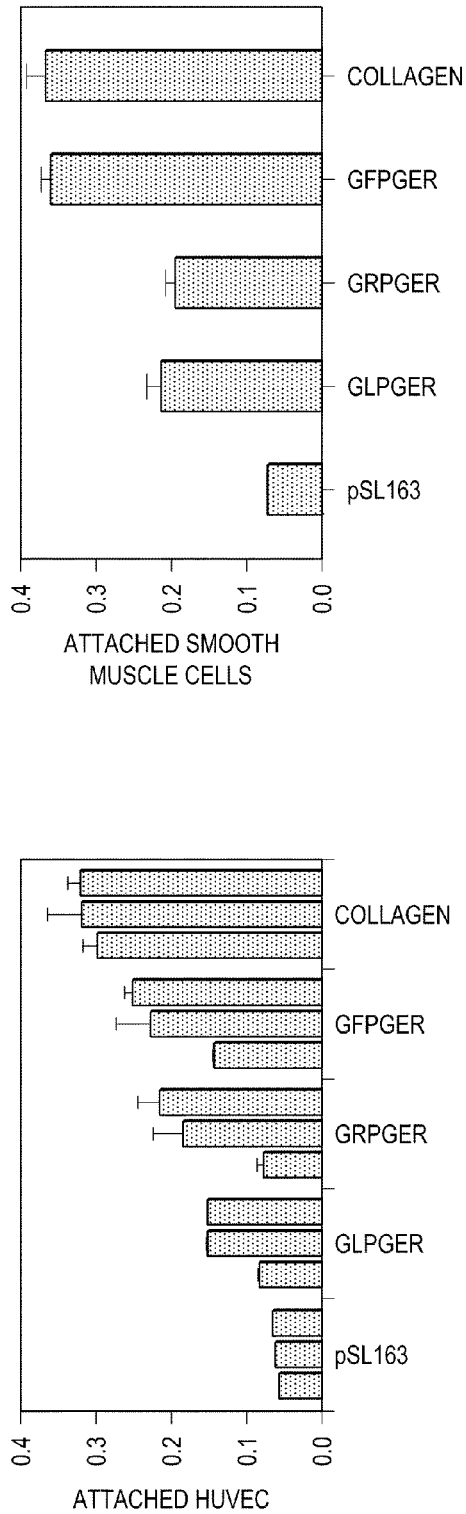
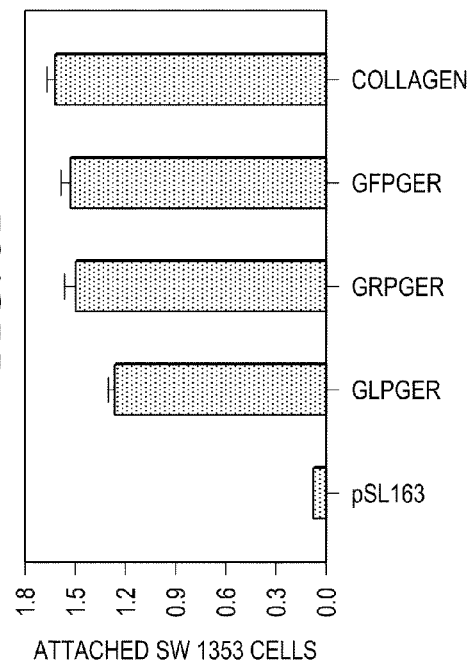

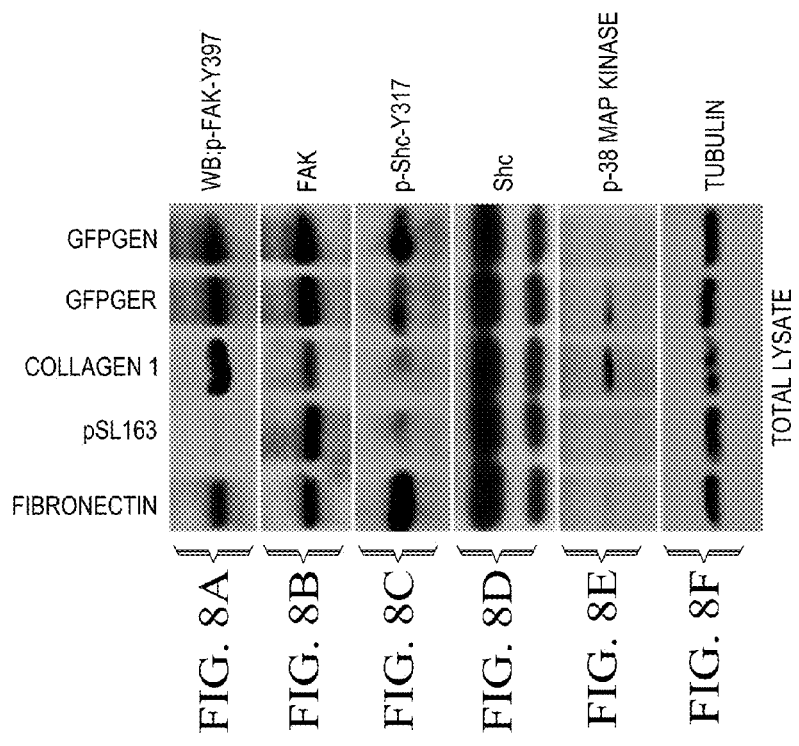
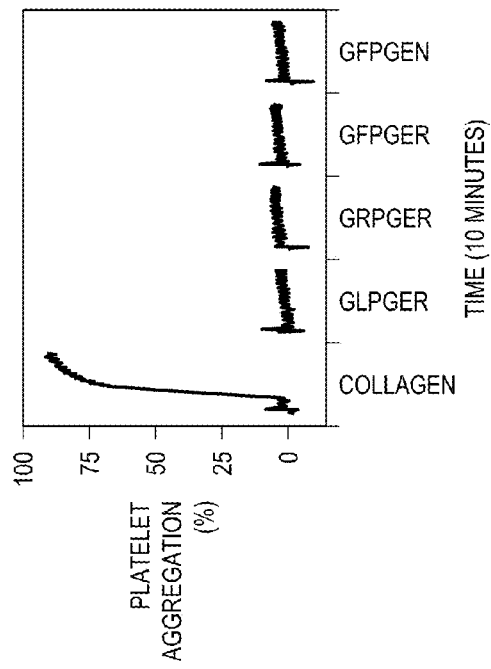
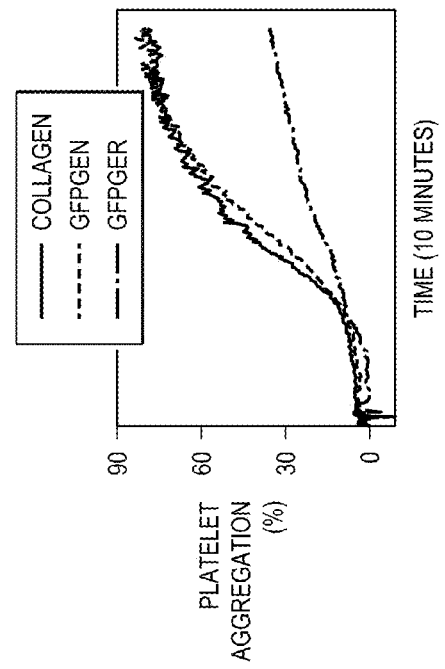

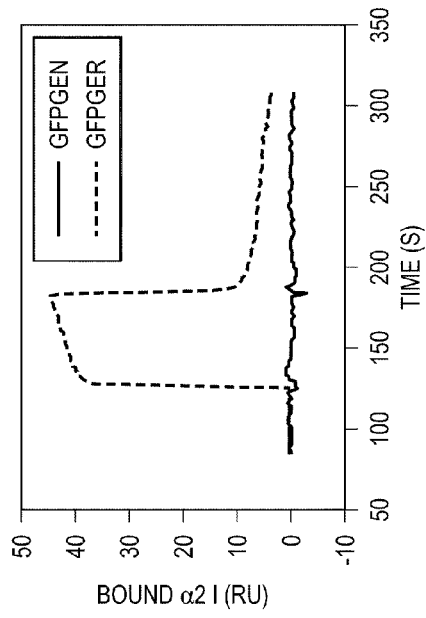
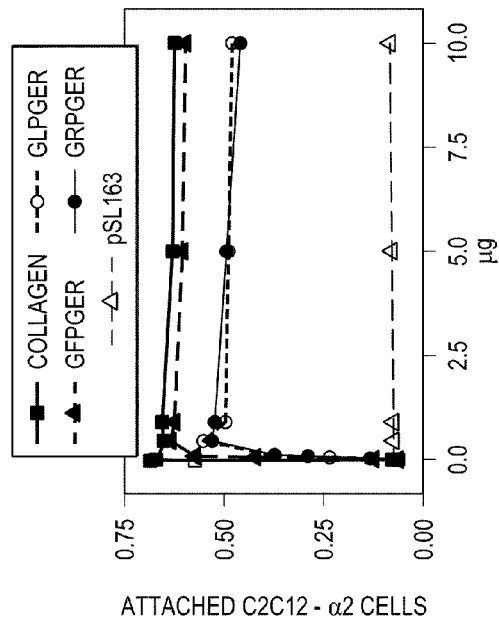
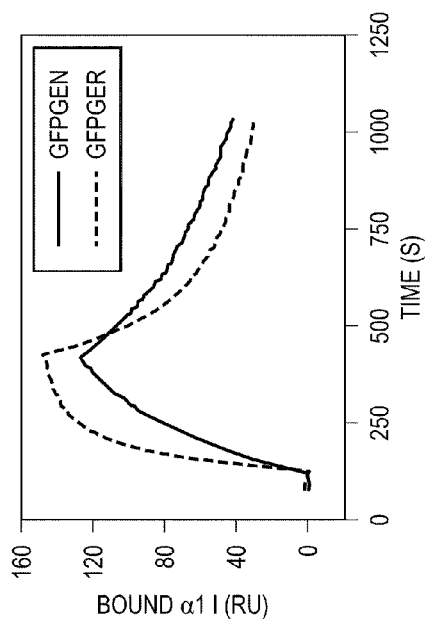
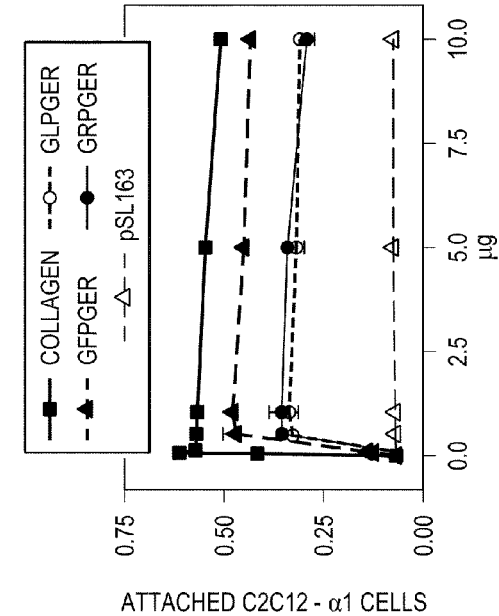
FIG. 7A
FIG. 7B

EC  SMC

SEQUENCE LISTING

<160> NUMBER OF SEQ ID NOS: 26

<210> SEQ ID NO 1
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (3)..(3)
<223> OTHER INFORMATION: Xaa is a hydroxyproline

<400> SEQUENCE: 1

Gly Phe Xaa Gly Glu Arg
1               5

<210> SEQ ID NO 2
<211> LENGTH: 6
<212> TYPE: PRT
<213> ORGANISM: artificial sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa is a hydroxyproline

<400> SEQUENCE: 2

Gly Leu Xaa Gly Glu Arg
1               5

<210> SEQ ID NO 3
<211> LENGTH: 6
<212> TYPE: PRT
<213> ORGANISM: artificial sequence
<220> FEATURE:
<223> OTHER INFORMATION: synthetic peptide

<400> SEQUENCE: 3

Gly Ala Ser Gly Glu Arg
1               5

<210> SEQ ID NO 4
<211> LENGTH: 6
<212> TYPE: PRT
<213> ORGANISM: artificial sequence
<220> FEATURE:
<223> OTHER INFORMATION: synthetic peptide

<400> SEQUENCE: 4

Gly Leu Pro Gly Glu Arg
1               5

<210> SEQ ID NO 5
<211> LENGTH: 6
<212> TYPE: PRT
<213> ORGANISM: artificial sequence
<220> FEATURE:
<223> OTHER INFORMATION: synthetic peptide

<400> SEQUENCE: 5

Gly Leu Pro Gly Glu Asn
1               5

<210> SEQ ID NO 6
<211> LENGTH: 6
<212> TYPE: PRT
<213> ORGANISM: artificial sequence
<220> FEATURE:
<223> OTHER INFORMATION: synthetic peptide

<400> SEQUENCE: 6

Gly Leu Pro Gly Glu Lys
1               5

<210> SEQ ID NO 7
<211> LENGTH: 6
<212> TYPE: PRT
<213> ORGANISM: artificial sequence
<220> FEATURE:
<223> OTHER INFORMATION: synthetic peptide

```
<400> SEQUENCE: 7

Gly Arg Pro Gly Glu Arg
1               5

<210> SEQ ID NO 8
<211> LENGTH: 6
<212> TYPE: PRT
<213> ORGANISM: artificial sequence
<220> FEATURE:
<223> OTHER INFORMATION: synthetic peptide

<400> SEQUENCE: 8

Gly Arg Pro Gly Glu Asn
1               5

<210> SEQ ID NO 9
<211> LENGTH: 6
<212> TYPE: PRT
<213> ORGANISM: artificial sequence
<220> FEATURE:
<223> OTHER INFORMATION: synthetic peptide

<400> SEQUENCE: 9

Gly Arg Pro Gly Glu Lys
1               5

<210> SEQ ID NO 10
<211> LENGTH: 6
<212> TYPE: PRT
<213> ORGANISM: artificial sequence
<220> FEATURE:
<223> OTHER INFORMATION: synthetic peptide

<400> SEQUENCE: 10

Gly Phe Pro Gly Glu Arg
1               5

<210> SEQ ID NO 11
<211> LENGTH: 6
<212> TYPE: PRT
<213> ORGANISM: artificial sequence
<220> FEATURE:
<223> OTHER INFORMATION: synthetic peptide

<400> SEQUENCE: 11

Gly Phe Pro Gly Glu Asn
1               5

<210> SEQ ID NO 12
<211> LENGTH: 6
<212> TYPE: PRT
<213> ORGANISM: artificial sequence
<220> FEATURE:
<223> OTHER INFORMATION: synthetic peptide

<400> SEQUENCE: 12

Gly Phe Pro Gly Glu Lys
1               5

<210> SEQ ID NO 13
<211> LENGTH: 12
<212> TYPE: PRT
<213> ORGANISM: artificial sequence
<220> FEATURE:
<223> OTHER INFORMATION: Synthetic peptide
<220> FEATURE:
<221> NAME/KEY: MISC_FEATURE
```

```
<222> LOCATION: (2)..(3)
<223> OTHER INFORMATION: Xaa is any amino acid
<220> FEATURE:
<221> NAME/KEY: MISC_FEATURE
<222> LOCATION: (5)..(5)
<223> OTHER INFORMATION: Xaa is Leu, Arg or Phe
<220> FEATURE:
<221> NAME/KEY: MISC_FEATURE
<222> LOCATION: (6)..(6)
<223> OTHER INFORMATION: Xaa is Pro
<220> FEATURE:
<221> NAME/KEY: MISC_FEATURE
<222> LOCATION: (8)..(8)
<223> OTHER INFORMATION: Xaa is Glu
<220> FEATURE:
<221> NAME/KEY: MISC_FEATURE
<222> LOCATION: (9)..(9)
<223> OTHER INFORMATION: Xaa is Arg, Lys or Asn
<220> FEATURE:
<221> NAME/KEY: MISC_FEATURE
<222> LOCATION: (11)..(12)
<223> OTHER INFORMATION: Xaa is any amino acid

<400> SEQUENCE: 13

Gly Xaa Xaa Gly Xaa Xaa Gly Xaa Xaa Gly Xaa Xaa
1               5                   10

<210> SEQ ID NO 14
<211> LENGTH: 12
<212> TYPE: PRT
<213> ORGANISM: artificial sequence
<220> FEATURE:
<223> OTHER INFORMATION: Synthetic peptide
<220> FEATURE:
<221> NAME/KEY: MISC_FEATURE
<222> LOCATION: (2)..(3)
<223> OTHER INFORMATION: Xaa is any amino acid
<220> FEATURE:
<221> NAME/KEY: MISC_FEATURE
<222> LOCATION: (11)..(12)
<223> OTHER INFORMATION: Xaa is any amino acid

<400> SEQUENCE: 14

Gly Xaa Xaa Gly Leu Pro Gly Glu Arg Gly Xaa Xaa
1               5                   10

<210> SEQ ID NO 15
<211> LENGTH: 12
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (2)..(3)
<223> OTHER INFORMATION: Xaa is any amino acid
<220> FEATURE:
<221> NAME/KEY: MISC_FEATURE
<222> LOCATION: (11)..(12)
<223> OTHER INFORMATION: Xaa is any amino acid

<400> SEQUENCE: 15

Gly Xaa Xaa Gly Leu Pro Gly Glu Asn Gly Xaa Xaa
1               5                   10

<210> SEQ ID NO 16
<211> LENGTH: 12
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (2)..(3)
```

```
<223> OTHER INFORMATION: Xaa is any amino acid
<220> FEATURE:
<221> NAME/KEY: MISC_FEATURE
<222> LOCATION: (11)..(12)
<223> OTHER INFORMATION: Xaa is any amino acid

<400> SEQUENCE: 16

Gly Xaa Xaa Gly Leu Pro Gly Glu Lys Gly Xaa Xaa
1               5                   10

<210> SEQ ID NO 17
<211> LENGTH: 12
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (2)..(3)
<223> OTHER INFORMATION: Xaa is any amino acid
<220> FEATURE:
<221> NAME/KEY: MISC_FEATURE
<222> LOCATION: (11)..(12)
<223> OTHER INFORMATION: Xaa is any amino acid

<400> SEQUENCE: 17

Gly Xaa Xaa Gly Arg Pro Gly Glu Arg Gly Xaa Xaa
1               5                   10

<210> SEQ ID NO 18
<211> LENGTH: 12
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (2)..(3)
<223> OTHER INFORMATION: Xaa is any amino acid
<220> FEATURE:
<221> NAME/KEY: MISC_FEATURE
<222> LOCATION: (11)..(12)
<223> OTHER INFORMATION: Xaa is any amino acid

<400> SEQUENCE: 18

Gly Xaa Xaa Gly Arg Pro Gly Glu Asn Gly Xaa Xaa
1               5                   10

<210> SEQ ID NO 19
<211> LENGTH: 12
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (2)..(3)
<223> OTHER INFORMATION: Xaa is any amino acid
<220> FEATURE:
<221> NAME/KEY: MISC_FEATURE
<222> LOCATION: (11)..(12)
<223> OTHER INFORMATION: Xaa is any amino acid

<400> SEQUENCE: 19

Gly Xaa Xaa Gly Arg Pro Gly Glu Lys Gly Xaa Xaa
1               5                   10

<210> SEQ ID NO 20
<211> LENGTH: 12
<212> TYPE: PRT
<213> ORGANISM: artificial sequence
<220> FEATURE:
```

```
<223> OTHER INFORMATION: synthetic peptide
<220> FEATURE:
<221> NAME/KEY: MISC_FEATURE
<222> LOCATION: (2)..(3)
<223> OTHER INFORMATION: Xaa is any amino acid
<220> FEATURE:
<221> NAME/KEY: MISC_FEATURE
<222> LOCATION: (11)..(12)
<223> OTHER INFORMATION: Xaa is any amino acid

<400> SEQUENCE: 20

Gly Xaa Xaa Gly Phe Pro Gly Glu Arg Gly Xaa Xaa
1               5                   10

<210> SEQ ID NO 21
<211> LENGTH: 12
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (2)..(3)
<223> OTHER INFORMATION: Xaa is any amino acid
<220> FEATURE:
<221> NAME/KEY: MISC_FEATURE
<222> LOCATION: (11)..(12)
<223> OTHER INFORMATION: Xaa is any amino acid

<400> SEQUENCE: 21

Gly Xaa Xaa Gly Phe Pro Gly Glu Asn Gly Xaa Xaa
1               5                   10

<210> SEQ ID NO 22
<211> LENGTH: 12
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (2)..(3)
<223> OTHER INFORMATION: Xaa is any amino acid
<220> FEATURE:
<221> NAME/KEY: MISC_FEATURE
<222> LOCATION: (11)..(12)
<223> OTHER INFORMATION: Xaa is any amino acid

<400> SEQUENCE: 22

Gly Xaa Xaa Gly Phe Pro Gly Glu Lys Gly Xaa Xaa
1               5                   10

<210> SEQ ID NO 23
<211> LENGTH: 6
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is Lau, Arg or Phe
<220> FEATURE:
<221> NAME/KEY: MISC_FEATURE
<222> LOCATION: (3)..(3)
<223> OTHER INFORMATION: Xaa is Pro
<220> FEATURE:
```

```
<221> NAME/KEY: MISC_FEATURE
<222> LOCATION: (5)..(5)
<223> OTHER INFORMATION: Xaa is Glu
<220> FEATURE:
<221> NAME/KEY: MISC_FEATURE
<222> LOCATION: (6)..(6)
<223> OTHER INFORMATION: Xaa is Arg, Lys or Asn

<400> SEQUENCE: 23

Gly Xaa Xaa Gly Xaa Xaa
1               5

<210> SEQ ID NO 24
<211> LENGTH: 12
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (2)..(3)
<223> OTHER INFORMATION: Xaa is any amino acid
<220> FEATURE:
<221> NAME/KEY: MISC_FEATURE
<222> LOCATION: (11)..(12)
<223> OTHER INFORMATION: Xaa is any amino acid

<400> SEQUENCE: 24

Gly Xaa Xaa Gly Leu Pro Gly Glu Arg Gly Xaa Xaa
1               5                   10

<210> SEQ ID NO 25
<211> LENGTH: 18
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (2)..(3)
<223> OTHER INFORMATION: Xaa is any amino acid
<220> FEATURE:
<221> NAME/KEY: MISC_FEATURE
<222> LOCATION: (11)..(12)
<223> OTHER INFORMATION: Xaa is any amino acid

<400> SEQUENCE: 25

Gly Xaa Xaa Gly Leu Pro Gly Glu Arg Gly Xaa Xaa Gly Leu Pro Gly
1               5                   10                  15

Glu Arg

<210> SEQ ID NO 26
<211> LENGTH: 26
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (2)..(3)
<223> OTHER INFORMATION: Xaa is any amino acid
<220> FEATURE:
<221> NAME/KEY: MISC_FEATURE
<222> LOCATION: (11)..(12)
<223> OTHER INFORMATION: Xaa is any amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: MISC_FEATURE
<222> LOCATION: (20)..(21)
<223> OTHER INFORMATION: Xaa is any amino acid
```

```
<400> SEQUENCE: 26

Gly Xaa Xaa Gly Leu Pro Gly Glu Arg Gly Xaa Xaa Gly Leu Pro Gly
1               5                   10                  15

Glu Arg Xaa Xaa Gly Leu Pro Gly Glu Arg
            20                  25
```

DESIGNER COLLAGENS AND USE THEREOF

CROSS-REFERENCE TO RELATED APPLICATION

This nonprovisional application claims benefit of priority under 35 U.S.C. §119(e) of provisional applications U.S. Ser. No. 61/335,432, filed Jan. 7, 2010, and U.S. Ser. No. 61/271,218, filed Jul. 17, 2009, the entirety of both of which are hereby incorporated by reference.

BACKGROUND OF THE INVENTION

1. Field of the Invention

The present invention relates generally to the field of computer-aided molecular modeling and interaction of extracellular matrix protein with receptors and cell signaling. More specifically, the present invention relates to recombinant "designer" collagens.

2. Description of the Related Art

Collagen is a major component of the extracellular matrix (ECM). At least 27 genetically different collagen types have been identified, each containing at least one dominant collagenous domain. These collagenous domains have a characteristic triple helix structure formed by repeating Gly-X-Y sequences in each participating chain where X often is Proline and Y is hydroxyproline. The collagen monomers often assemble into more complex structures of varying organizations such as fibrils (types I-III, V and XI), networks (types IV, VIII and X) and beaded filaments (type VI). The fibrillar collagen types I and III are the major structural components of the extracellular matrix of skin, cardiac and vascular tissues, whereas type II collagen is a major structural component of cartilage. In addition to contributing to the structural integrity of the tissues, collagens also affect cell behavior through interactions with other matrix proteins and cellular receptors.

The integrins are a family of heterodimeric cell surface receptors involved in cell-cell and cell-substrate adhesion. They act as bridging molecules that link intracellular signaling molecules to the extracellular matrix through bi-directional signaling and control cell behaviour and tissue architecture. Four integrins, $\alpha_1\beta_1$, $\alpha_2\beta_1$, $\alpha_{10}\beta_1$ and $\alpha_{11}\beta_1$ have been shown to bind collagens. Collagen integrin interactions play a role in normal and pathological physiology and directly affect cell adhesion, migration, proliferation and differentiation as well as angiogenesis, platelet aggregation and extracellular matrix assembly. However, the precise molecular mechanisms that lead to these activities are not understood.

Collagen binding by the four integrins is mediated by a ~200 amino acids long so-called inserted domain (I domain) found between blades 2 and 3 of the β-propeller domain of the α chains. All four I domains ($\alpha_1$I, $\alpha_2$I, $\alpha_{10}$I, $\alpha_{11}$I) contain a metal ion-dependent adhesion site (MIDAS) that is required for coordinating a divalent cation and is essential for collagen binding. Synthetic collagen peptides containing the type I collagen derived sequences, GFOGER (SEQ ID NO: 1) or GLOGER (SEQ ID NO: 2) bind with high affinity to $\alpha_1$I, $\alpha_2$I and $\alpha_{11}$I; furthermore, synthetic peptides containing these sequences inhibit the binding of I domains to intact collagens. The crystal structures of apo-$\alpha_1$I and $\alpha_2$I in complex with a collagen peptide containing the GFOGER (SEQ ID NO: 1) sequence have been solved and showed that the apo-$\alpha_1$I adopted an inactive "closed" conformation and the ligand bound $\alpha_2$I, an active "open" conformation. The Glu residue in the collagen peptide was shown in the structure of the complex to directly interact with a $Mg^{2+}$ ion co-ordinated by the MIDAS motif and the Arg residue forms a salt bridge with $D_{219}$ in $\alpha_2$I. The importance of the GER sequence in collagen for integrin binding was confirmed by mutagenesis studies, which showed that replacing Glu in the collagen peptide with an Asp residue completely abolished the binding whereas replacing the Arg with a Lys residue reduced the binding by 50%. The Phe residue in the collagen sequence appeared to participate in hydrophobic interactions with $\alpha_2$I and could be replaced by Leu. Both GFOGER (SEQ ID NO: 1) and GLOGER (SEQ ID NO: 2) bind to $\alpha_1$I and $\alpha_2$I (Xu et al., 2000). However, changing the Phe residue to a Met or an Ala reduced the apparent affinity of I domains (Siljander et al., 2004). GASGER (SEQ ID NO: 3) was also reported to be recognized by the I domains but bound with lower affinity than GFOGER (SEQ ID NO: 1) and GLOGER (SEQ ID NO: 2) (Zhang et al., 2003; Siljander et al., 2004; Xu et al., 2000). Therefore, GFOGER (SEQ ID NO: 1) and GLOGER (SEQ ID NO: 2) are the only two known collagen-derived sequence motifs that support high affinity binding by the collagen-binding I domains. However, the GFOGER (SEQ ID NO: 1) and GLOGER (SEQ ID NO: 2) motifs are absent in some collagens such as human type III collagen. Additionally, CHO cell expressing $\alpha_1\beta_1$ and $\alpha_2\beta_1$ could adhere and spread on human type III collagen and furthermore, the recombinant proteins of $\alpha_1$I and $\alpha_2$I could bind to this collagen type.

Collagen and its derivative, gelatin, have been used in medical, pharmaceutical and consumer products for more than 100 years. Collagen biomaterials approved for use in humans are predominantly obtained from animal sources. Animal derived collagens have a risk of immunogenecity and have a risk of contamination with pathogens such as viruses and prions, which cause the human form of mad cow disease. These limitations can be overcome by recombinant protein expression technologies. Several groups have generated recombinant collage type I or III from expression systems utilizing, mammalian, insect, yeast, and plant cells. However, these materials are not currently in clinical trials. These materials have several limits including high cost and low yields. Regardless of how these collagens are obtained, the collagen molecule contains molecular properties that differ widely in function. The introduction of this plethora of different properties can cause an adverse reaction on a molecular level that can lead to scar tissue formation, immunogenic effects, adhesion production, and thrombosis. Thus, there is a need in the art for collagen biomaterials that are devoid of or having reduced undesirable effects including risk of immunogenicity. The present invention fulfills this long-standing need and desire in the art.

SUMMARY OF THE INVENTION

The present invention is directed to a recombinant synthetic collagen, said collagen containing a triple helical backbone protein produced in a prokaryotic expression system. The present invention is directed to a recombinant synthetic collagen, said collagen containing a triple helical backbone protein produced in a prokaryotic expression system wherein said protein contains at least one 'inserted' biologically active sequence(s).

The present invention is directed to designer collagens engineered to have a single or subset of certain properties. Designer collagens produced in a prokaryotic expression system are easy to scale-up using current industrial pipelines with low development costs. Also, designer collagens can be genetically customized quickly to exhibit desired features for a target market niche. Other and further aspects, features, and advantages of the present invention will be apparent from the following description of the presently preferred embodiments of the invention. These embodiments are given for the purpose of disclosure.

BRIEF DESCRIPTION OF THE DRAWINGS

FIG. 13A shows Coomassie-stained 12% SDS-PAGE analysis of functionalized Designer Collagens (P163 Control, P163-F, GFPGER-F, GFPGEN-F) with and without heat denaturation. FIG. 13B shows that functionalized Designer Collagens demonstrate a typical peak at 220 nm in the circular dichroism (CD) spectra indicative of a triple helical structure. FIG. 13C shows a representative thermal transition of functionalized Designer Collagen monitored at 220 nm indicating an alteration in protein conformation at ~37° C.

DETAILED DESCRIPTION OF THE INVENTION

Figure 1:
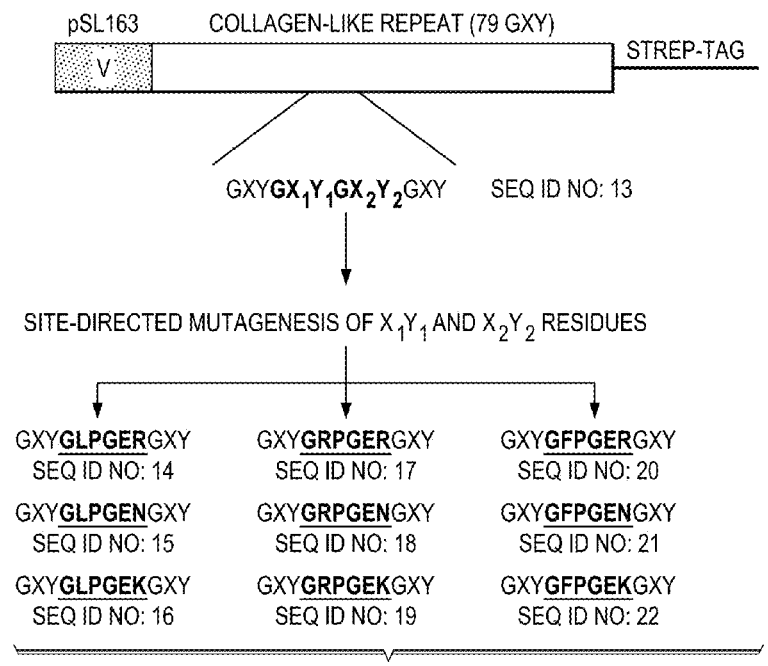
FIG. 1 shows pSL163, a collagen-like protein from Group A *Streptococcus* used as a template to insert receptor-binding motifs by site-directed mutagen Collagen type I.

The present invention has identified the design, production and use of "designer collagens". Designer Collagens encompass the following characteristics: a triple helical backbone protein produced in a prokaryotic expression system with an 'inserted' biologically active sequence(s). The triple helical backbone is derived from a Streptococcal protein and is considered collagen-like. 'Inserted' sequences are generated by standard molecular biologically techniques, including computer modeling and site-directed mutagenesis. Biologically active sequences impart a specific function to another molecule or cell with a desired effect. An example of an 'inserted' biologically active sequence is an integrin binding motif.

Collagen is a major component of the extracellular matrix and it functions to provide tensile strength to tissues as well as influence cell behavior through interactions with cellular receptors. Collagen has been used as a biomaterial in medical, pharmaceutical and consumer products for more than one hundred years. Collagen biomaterials approved for use in humans are predominantly derived from animal sources and have certain limits. These limitations can be overcome by advances in collagen-cell interactions and recombinant protein expression technologies. Designer Collagens as biomaterials have the potential to improve collagen's use in current markets and also Designer Collagens may be used in markets where collagen is not considered an optimal biomaterial. Designer Collagens are highly purified, fully characterized, and can be genetically customized to exhibit desired features for particular applications of interest including presentation of receptor binding motifs.

Thus, in one embodiment of the present invention, there is provided a recombinant synthetic collagen. This recombinant synthetic collagen contains a triple helical backbone protein produced in a prokaryotic expression system. Preferably, the protein contains at least one 'inserted' biologically active sequence(s). In one preferred form, the recombinant synthetic collagen has a triple helical backbone derived from a Streptococcal protein. Preferably, the Streptococcal protein contains a collagen-like repeat of $GXYGX_1Y_1GX_2Y_2GXY$ (SEQ ID NO: 13) and wherein the recombinant synthetic collagen is created by changing X1 position to L, R, or F residues or Y2 position to R, K, or N residues. In one preferred form, the biologically active sequence is an integrin binding motif. Generally, the recombinant synthetic collagen of the present invention are capable of binding to integrins α1β1 and/or α2β1 without hydroxyproline.

In the recombinant synthetic collagen of the present invention, representative biologically active sequences are GLPGER (SEQ ID NO: 4), GLPGEN (SEQ ID NO: 5), GLPGEK (SEQ ID NO: 6), GRPGER (SEQ ID NO: 7), GRPGEN (SEQ ID NO: 8), GRPGEK (SEQ ID NO: 9), GFPGER (SEQ ID NO: 10), GFPGEN (SEQ ID NO: 11), or GFPGEK (SEQ ID NO: 12). In one form, the recombinant synthetic collagen of the present invention are produced in a bacterial expression system deficient in post-translational modification.

Particularly, in a related embodiment, the present invention therefore provides the specific biologically active motif sequences of the recombinant synthetic collagen shown in GLPGER (SEQ ID NO: 4), GLPGEN (SEQ ID NO: 5), GLPGEK (SEQ ID NO: 6), GRPGER (SEQ ID NO: 7), GRPGEN (SEQ ID NO: 8), GRPGEK (SEQ ID NO: 9), GFPGER (SEQ ID NO: 10), GFPGEN (SEQ ID NO: 11), and GFPGEK (SEQ ID NO: 12).

As is described in detail infra, the recombinant synthetic collagen of the present invention may be designed to have a variety of functions. For example, the collagen containing sequences GLPGER (SEQ ID NO: 4), GRPGER (SEQ ID NO: 7), or GFPGER (SEQ ID NO: 10)), support adherence of both $\alpha 1\beta 1$ and $\alpha 2\beta 1$, spreading of endothelial cells, fibroblasts, chondrocytes, and smooth muscle cells. Also, the collagen containing sequence GFPGER (SEQ ID NO: 10) support adherence and spread of mesenchymal stem cells and adipocyte stem cells. In addition, the collagen containing sequences GFPGER (SEQ ID NO: 10) and GFPGEN (SEQ ID NO: 11) support adherence and spread of mesenchymal stem cells In one embodiment, the present invention provides a recombinant synthetic collagen containing a GFPGEN sequence selectively bind to integrin $\alpha 1\beta 1$, but not to $\alpha 2\beta 1$. This recombinant synthetic collagen supports adherence of endothelial cells, fibroblasts, and chondrocytic cells, but does not support adherence of smooth muscle cells.

In another embodiment, the present invention provides a recombinant synthetic collagen containing GLPGER, GRPGER, GFPGER, or GFPGEN sequences. Such recombinant synthetic collagens do not aggregate platelets and are non-thrombogenic.

In another embodiment, the present invention provides a recombinant synthetic collagen containing a GFPGER (SEQ ID NO: 10) sequence. Such a recombinant synthetic collagen inhibits collagen-induced platelet aggregation. In another embodiment, the present invention provides a recombinant synthetic collagen containing a GFPGEN (SEQ ID NO: 11) sequence. Such a recombinant synthetic collagen does not inhibit collagen-induced platelet aggregation. In another embodiment, the present invention provides a recombinant synthetic collagen containing one, two, three, four and/or five multiple cell binding motifs. Such recombinant synthetic collagens have a density dependent increase in integrin affinity, cell binding, and cell migration. In another embodiment, the present invention provides a recombinant synthetic collagen containing one, two, three, four and/or five GLPGER cell binding motifs.

In another embodiment, the present invention provides a recombinant synthetic collagen wherein said collagen is affixed to or linked in a chemical manner to a scaffold with intrinsic tensile properties. A person having ordinary skill in this art would readily recognize useful scaffolds but representative examples include but are not limited to PEG-containing hydrogels, ECM components, and mesh materials.

In another embodiment, the present invention provides a recombinant synthetic collagen containing a triple helical backbone protein produced in a prokaryotic expression system. In another embodiment, the present invention provides a recombinant synthetic collagen further comprising an insert selected from the group consisting of but not limited to bone sialoprotein binding sequences, integrins $\alpha 10\beta 1$ and $\alpha 11\beta 1$ binding sequences, and an extracellular matrix constituent.

The following example(s) are given for the purpose of illustrating various embodiments of the invention and are not meant to limit the present invention in any fashion.

EXAMPLE 1

Designer Collagens Produced in a Bacterial Expression System Bind to Integrin $\alpha 1\beta 1$ and/or $\alpha 2\beta 1$ and as Substrates Support Adherence and Spreading of Multiple Cell Types Post-translational modification of collagen to include hydroxyproline residues is important to stabilize the triple helical conformation of collagen. Hydroxyproline has also been implicated in collagen binding to integrins, including $\alpha 1\beta 1$ and $\alpha 2\beta 1$. For example, unhydroxylated collagen produced in plants shows reduced binding affinity for integrin $\alpha 1\beta 1$ and failed to bind $\alpha 2\beta 1$. Adhesion of platelets on unhydroxylated collagen via integrin $\alpha 2\beta 1$ is weaker than on hydroxylated collagen and unhydroxylated collagen fails to induce platelet aggregation. This data suggests that hydroxyproline on collagen is essential for high affinity binding to $\alpha 1\beta 1$ and $\alpha 2\beta 1$. A molecular mechanism detailing the binding differences of unhydroxylated and hydroxylated collagen to integrins $\alpha 1\beta 1$ and $\alpha 2\beta 1$ is unknown. Therefore, the present invention describes new materials capable of binding to integrins $\alpha 1\beta 1$ and $\alpha 2\beta 1$ without hydroxyproline.

Designer Collagens with 'inserted' biologically active sequences, GLPGER (SEQ ID NO: 4), GLPGEN (SEQ ID NO: 5), GLPGEK (SEQ ID NO: 6), GRPGER (SEQ ID NO: 7), GRPGEN (SEQ ID NO: 8), GRPGEK (SEQ ID NO: 9), GFPGER (SEQ ID NO: 10), GFPGEN (SEQ ID NO: 11), GFPGEK (SEQ ID NO: 12), were produced in a bacterial expression system, which is deficient in post-translational modification, including hydroxylation of proline and lysine residues. Designer Collagens with 'inserted' sequences (GLPGER (SEQ ID NO: 4), GRPGER (SEQ ID NO: 7), and GFPGER (SEQ ID NO: 10)), however, support adherence of both $\alpha 1\beta 1$ and $\alpha 2\beta 1$ regardless of the lack of hydroxyproline. This conclusion was reached by ELISA-based assays and Surface Plasmon Resonance analysis. Since many cell types express $\alpha 1\beta 1$ and $\alpha 2\beta 1$, Designer Collagens support adherence and spreading of different cell types including endothelial cells, fibroblasts, chondrocytes, and smooth muscle cells. Cell adherence was quantified and cell morphology was evaluated using fluorescence microcopy techniques.

EXAMPLE 2

Designer Collagens with a GFPGEN Residue Sequence Selectively Bind to Integrin $\alpha 1\beta 1$, but not to $\alpha 2\beta 1$ Selective binding was determined by ELISA-based assays and Surface Plasmon Resonance analysis. The Designer Collagen with GFPGEN as a substrate supports adherence of endothelial cells, fibroblasts, and chondrocytic cells, but does not support adherence of smooth muscle cells.

EXAMPLE 3

The Designer Collagens are Non-Thrombogenic

Collagen is one of several agonists that can activate platelets by the binding of specific sequences, GFOGER and/or GLOGER, to integrin $\alpha 2\beta 1$ on platelets. Designer Collagens with residue motifs GLPGER, GRPGER, GFPGER, and GFPGEN were tested in platelet aggregation assays to determine whether they activate platelets. Designer Collagens do not aggregate platelets at 10-fold higher concentrations than native collagen in platelet aggregation assays. This data indicates that these Designer Collagens are completely non-thrombogenic although they contain sequences that are derived from native collagen, which act as an agonist for platelet aggregation.

Designer Collagens were tested in platelet aggregation inhibition assays to determine whether they can inhibit collagen-induced platelet aggregation. Designer Collagens with GFPGER (SEQ ID NO: 10) inhibits collagen-induced platelet aggregation indicating that Designer Collagens with GFPGER competes with native collagen to bind $\alpha 2\beta 1$ without aggregating platelets. The Designer Collagen with GFPGER is an antagonist to inhibit collagen-induced platelet aggregation via the blocking of $\alpha 2\beta 1$ integrin. The Designer Collagen with a GFPGEN (SEQ ID NO: 11) residue sequence did not inhibit collagen-induced platelet aggregation since the Designer Collagen only binds to integrin $\alpha 1\beta 1$ that is not normally expressed on platelets. The Designer Collagen with GFPGEN would be an ideal biomaterial for vascular applications.

The introduction of one, two, three, four and/or five multiple cell binding motifs results in a density dependent increase in integrin affinity, cell binding, and cell migration. This was determined by comparing Designer Collagens with one, two, three, four and five GLPGER cell binding motifs. Integrin affinity was assessed by surface plasmon resonance. Cell binding and migration was demonstrated with human umbilical vein endothelial cells.

EXAMPLE 4

Construction of Designer Collagens

Bacterial collagen-like proteins derived from Group A *Streptococcus* have been used as a template to produce Designer Collagens with inserted motifs with specific functions. The functional motifs have receptor binding activities through an interaction with collagen binding integrins, $\alpha 1\beta 1$ and $\alpha 2\beta 1$. These proteins are termed Designer Collagens and they include the following characteristics: humanized collagen fragments or fragments generated through computer modeling that are inserted into a bacterial collagen-like backbone and produced in a prokaryotic expression system. pSL163, a collagen-like protein from Group A *Streptococcus* was used as a template to insert receptor-binding motifs. Site-directed mutagenesis was performed to change X1 position to L, R, or F residues or and X2 position to R, K, or N residues (FIG. 1). These constructs were expressed in *E. coli* and recombinant proteins were purified. The library of Designer Collagens contains recombinant proteins with the following receptor-binding motifs: GLPGER, GRPGER, GFPGER, GLPGEN, GRPGEN, GFPGEN, GLPGEK, GRPGEK, and GFPGEK. The present invention characterized the identity and purity of these recombinant proteins using SDS-PAGE, Western-blot analysis, and Circular Dichroism spectroscopy. All of these proteins formed a triple helical structure. The binding of the Designer Collagens with residue sequences of GLPGER, GRPGER, GFPGER, GLPGEN, GRPGEN, GFPGEN, GLPGEK, GRPGEK, and GFPGEK, to $\alpha 1$ and $\alpha 2$ I domains were examined in ELISA-based assays. The binding of Designer Collagens with residue sequences of GFPGER, GRPGER, GLPGER, and GFPGEN was tested using Surface Plasmon Resonance analysis using a BIAcore 3000 machine. C2C12 cells, derived from a mouse myoblast cell line, lack expression of the $\alpha$-subunit of collagen binding integrins $\alpha 1\beta 1$, $\alpha 2\beta 1$, $\alpha 10\beta 1$, and $\alpha 11\beta 1$. These cells can be utilized to determine the individual contribution of integrin binding to a substrate. The $\alpha$ subunits are stably expressed in individual cells line, C2C12-$\alpha 1$ and C2C12-$\alpha 2$. Whether immobilized Designer Collagens in the library support adherence and spreading of these cell types was tested. In addition, endothelial cells, fibroblasts, chondrocytic cells, and smooth muscle cells were tested in adherence and spreading assays. The ability of cells to migrate on immobilized Designer Collagens in 96 well plates, tissue culture chamber slides, or modified migration assays plates was determined. The Designer Collagens were also tested in platelet aggregation assays to determine whether the Designer Collagens bind and activate platelets.

Based on the experimental data, proteins with unique and novel characteristics were demonstrated. The Designer Collagen with GFPGEN residues is a biomaterial for vascular applications. The Designer Collagen with GFPGER residues is an antagonist, which blocks interaction of collagen with $\alpha 2\beta 1$ on platelets. The Designer Collagen with GFPGER residues can interact with $\alpha 1\alpha 1$ and $\alpha 2\beta 1$ and therefore may be a cell recruiting molecule with applications in angiogenesis, wound healing, and orthopedics.

Designer Collagens need to be biocompatible and non-immunogenic in humans, which will be addressed using appropriate animal models before clinical trials. Modification of certain portions of Designer Collagen may be required for appropriate use in humans. Designer Collagens are proteins that do not naturally form higher ordered structures such as fibers; therefore, Designer Collagens lack intrinsic tensile properties or a three-dimensional structure. Designer Collagens may need to be affixed to or linked in a chemical manner to a scaffold with intrinsic tensile properties. Currently, PEG-containing hydrogels, ECM components, and mesh materials may be used as scaffolds.

EXAMPLE 5

Figure 2A:
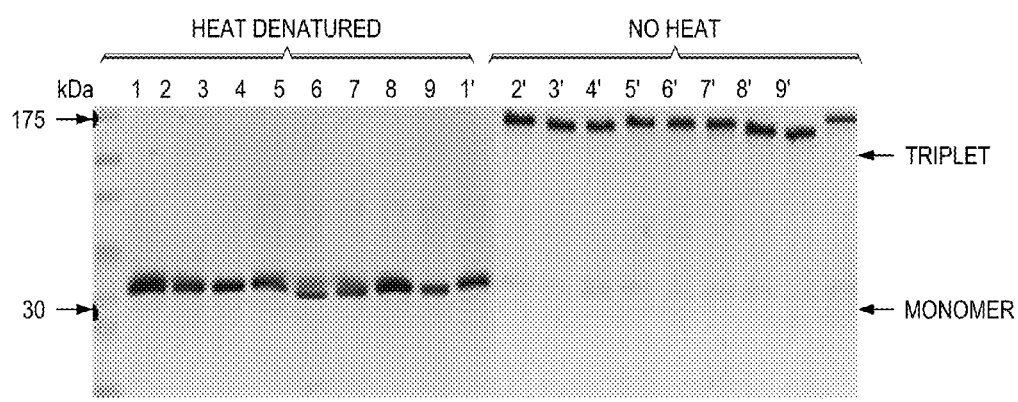
Figure 2B:
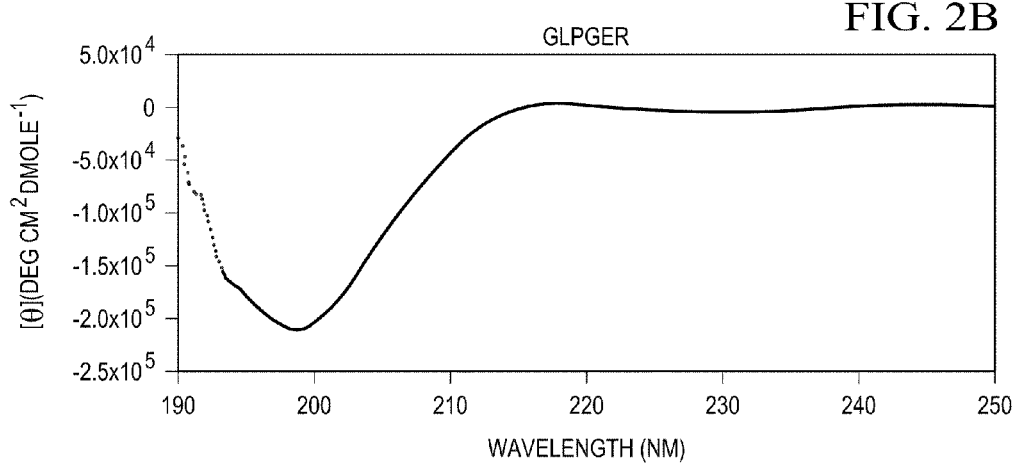
Figure 2C:
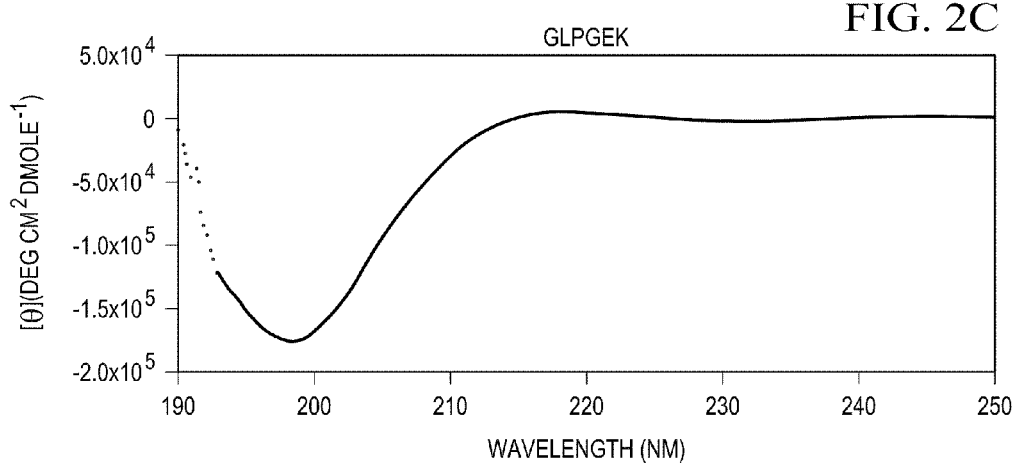
Figure 2D:
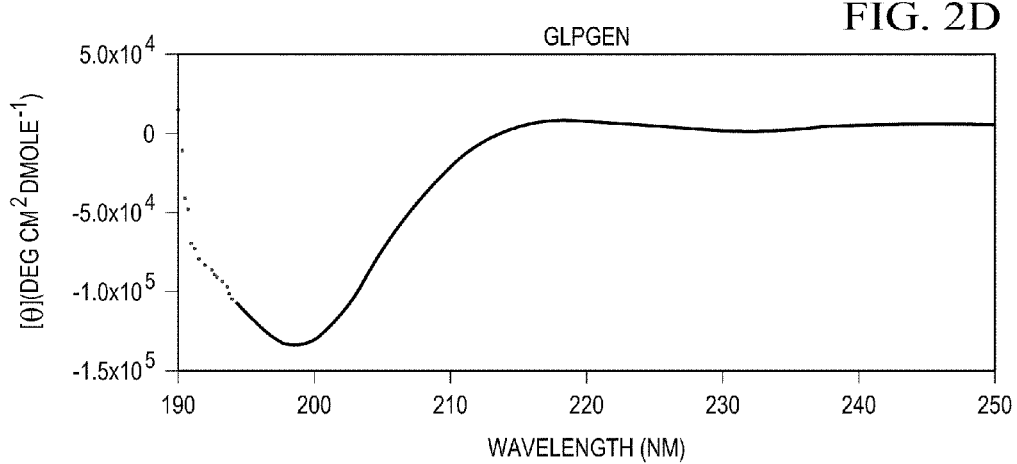
Figure 2E:
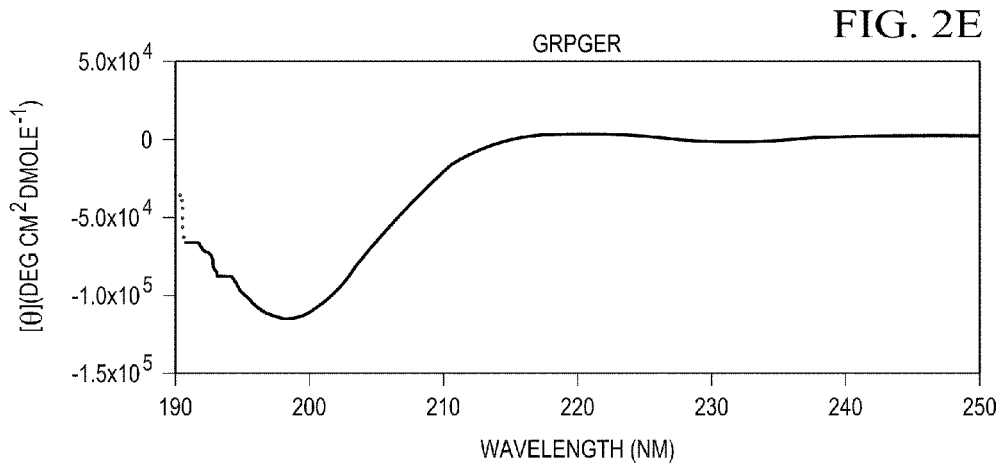
Figure 2F:
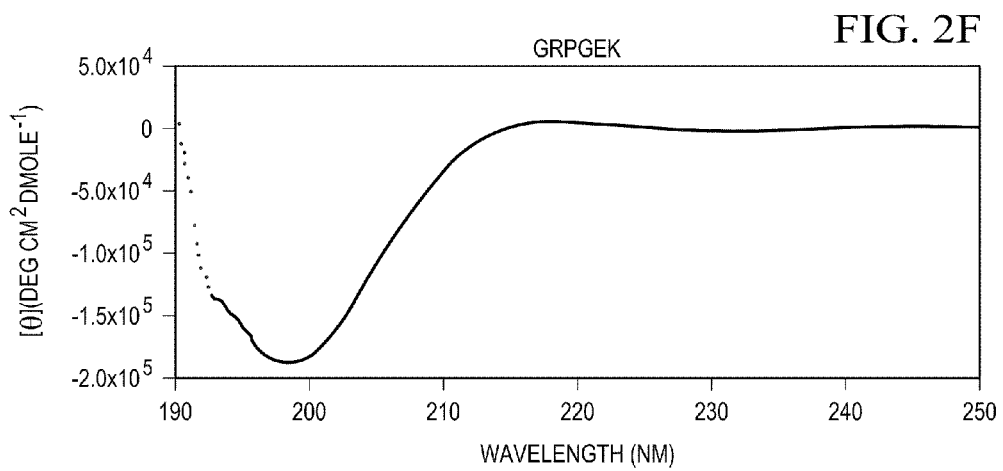
Figure 2G:
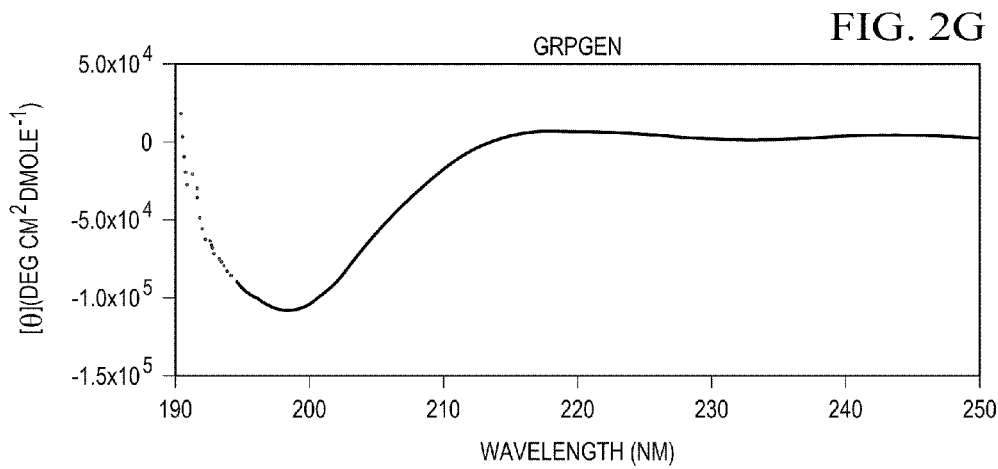
Figure 2H:
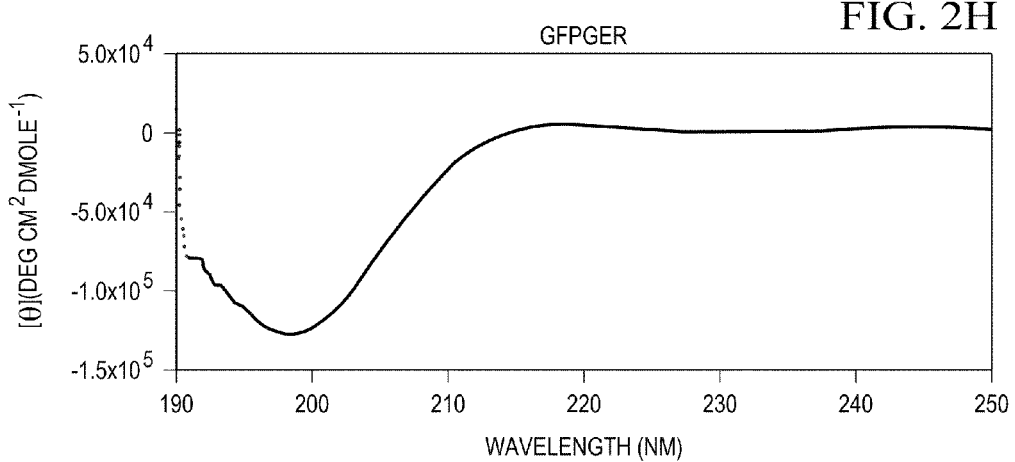
Figure 2I:
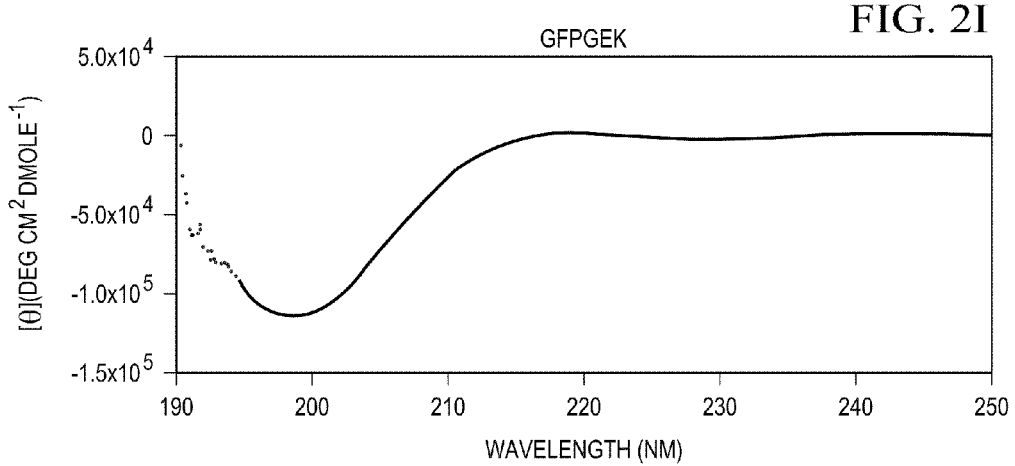
Figure 2J:
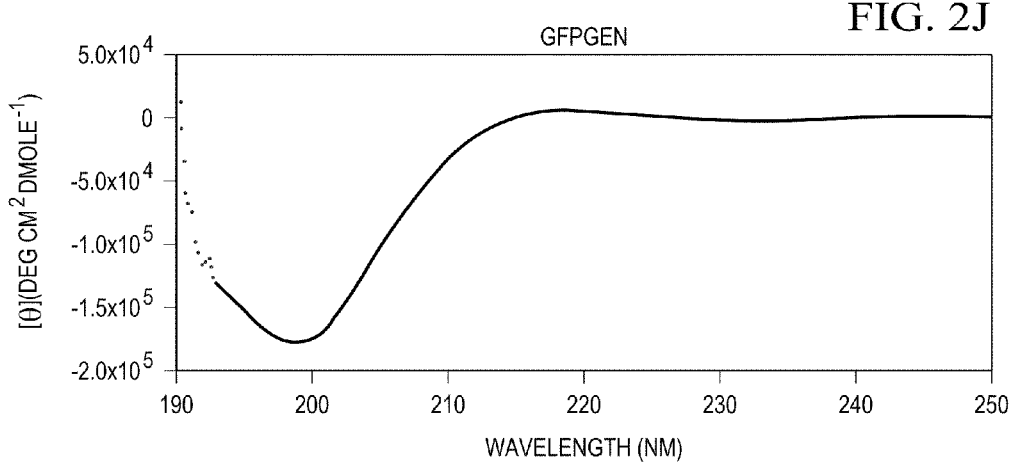
Figure 2K:
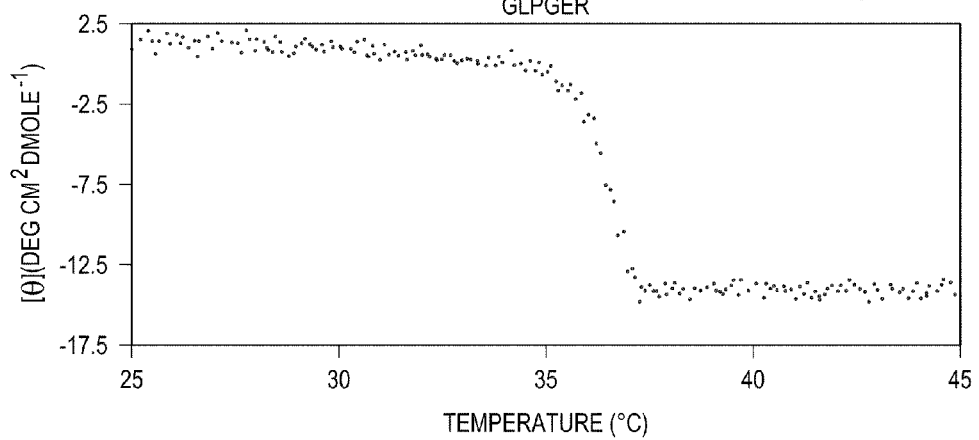
Figure 2L:
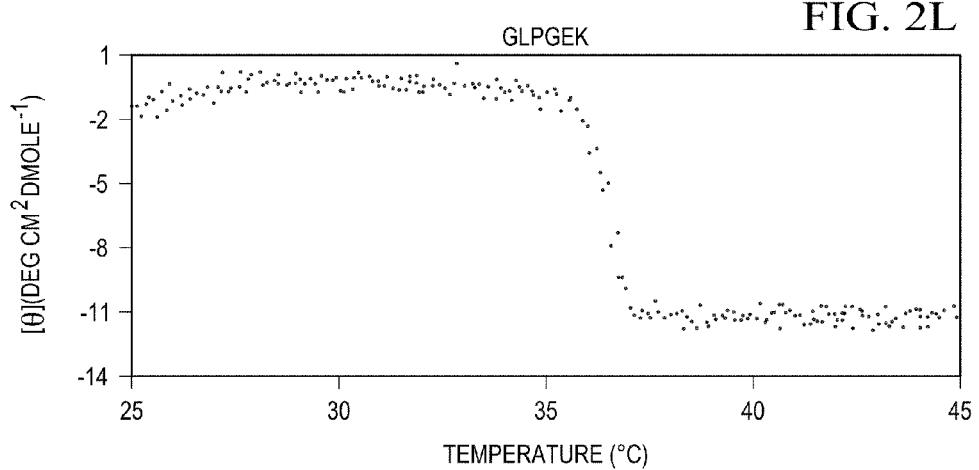
Figure 2M:
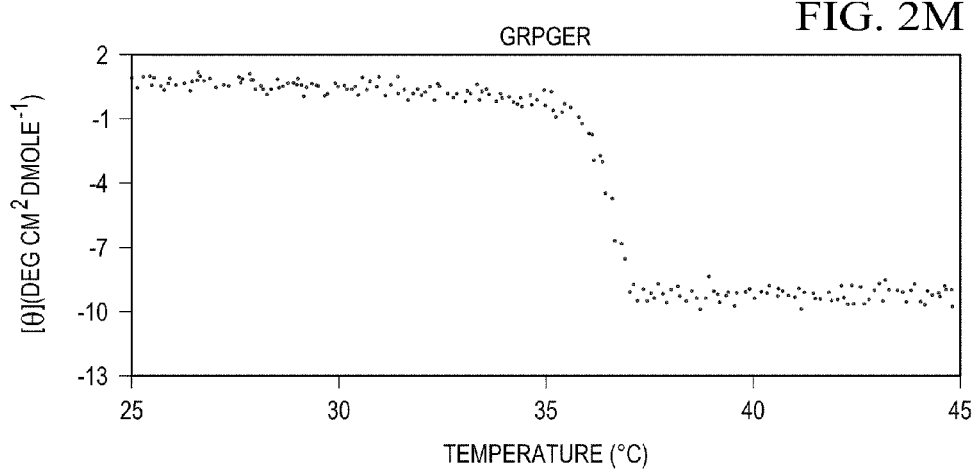
Figure 2N:
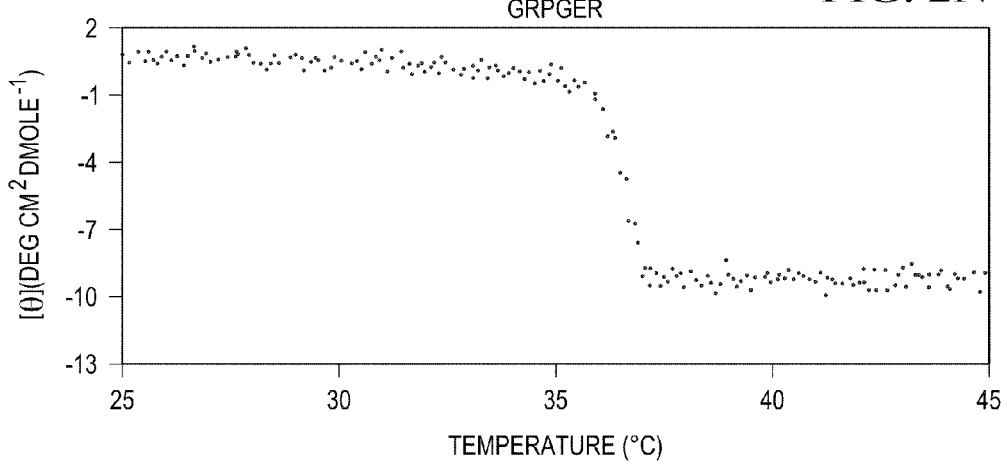
Figure 2O:
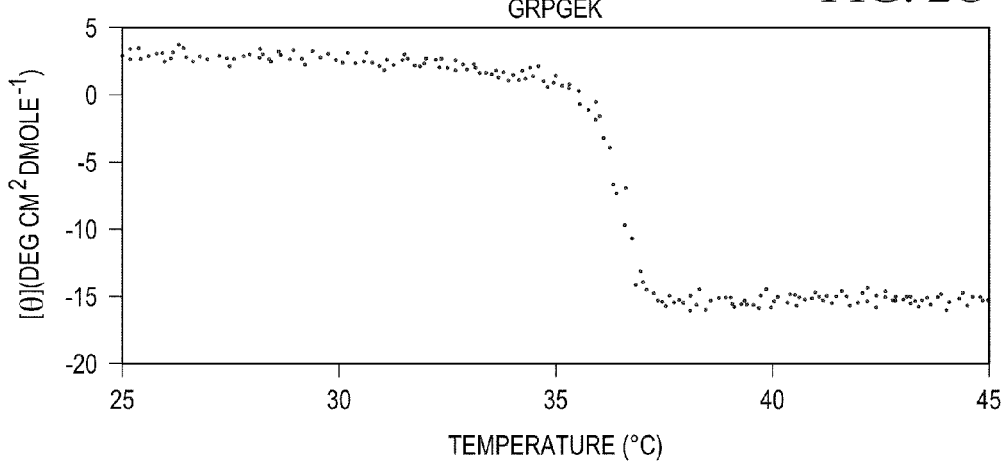
Figure 2P:
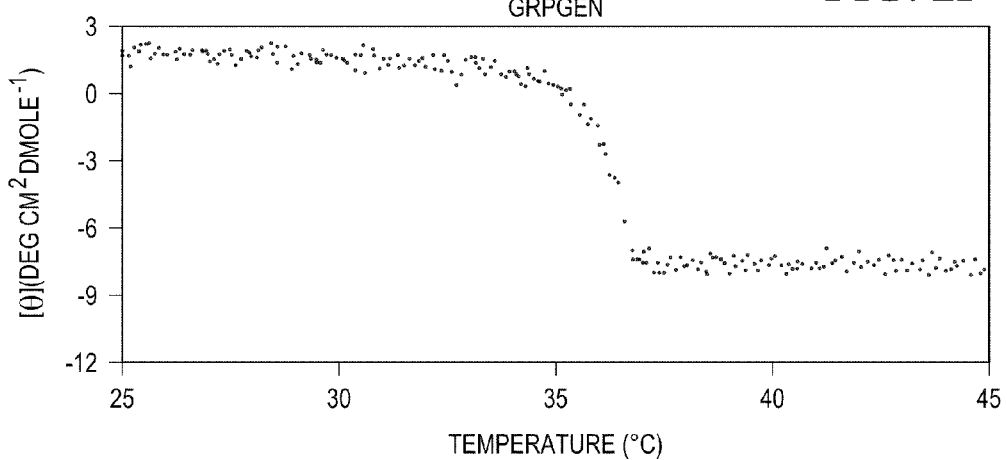
Figure 2Q:
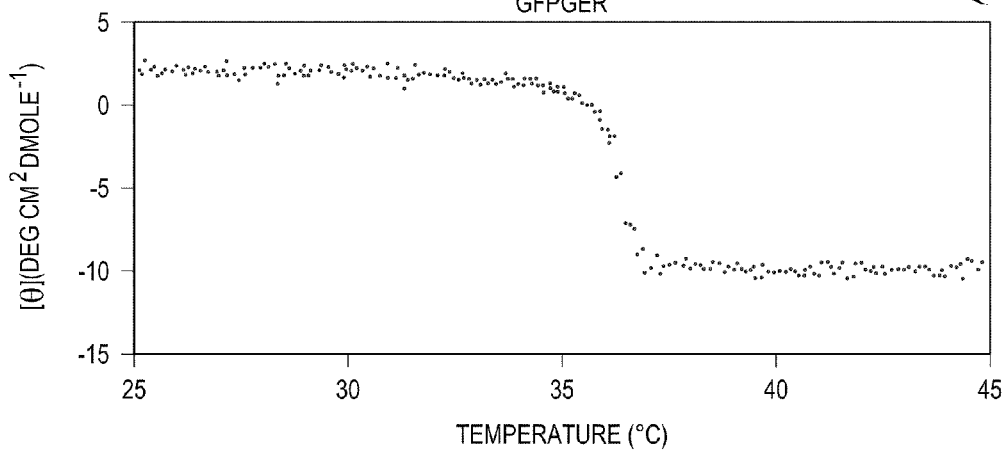
Figure 2R:
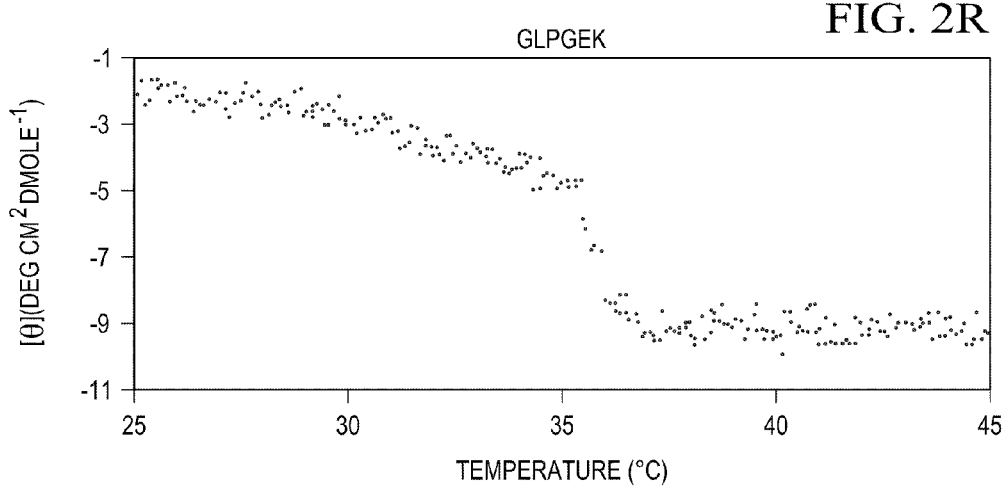
Figure 2S:
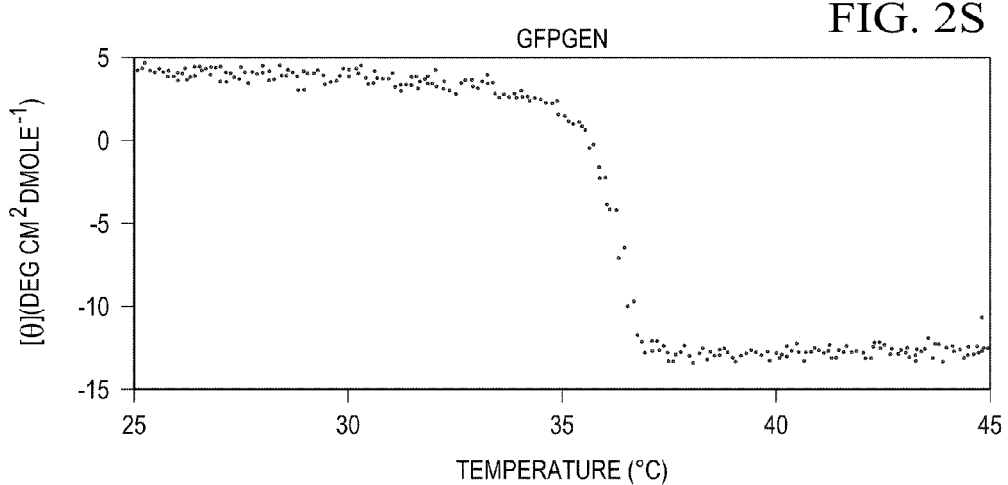

Recombinant Designer Collagens Expressed in a Bacterial System Exhibit a Triple Helical Structure at Physiological Temperatures pSL163 (P163), a construct containing bacterial collagen-like sequences that form a triple helix, was used as a backbone. To generate receptor-binding motifs including, GLPGER, GLPGEN, GLPGEK, GRPGER, GRPGEN, GRPGEK, GFPGER, GFPGEN, GFPGEK, site-directed mutagenesis was used to 'insert' these cell-binding sites into the pSL163 backbone (FIG. 1). The constructs were expressed in *E. coli* and recombinant proteins were purified. As shown in FIG. 2A, purified collagen-like proteins have over 95% purity and form a triple helical structure under non-denatured conditions in 12% SDS-PAGE. Residue sequences correspond to the following numbered system (1-GLPGER, 2-GLPGEN, 3-GLPGEK, 4-GRPGER, 5-GRPGEN, 6-GRPGEK, 7-GFPGER, 8-GFPGEN, 9-GFPGEK). Far UV Circular Dichroism spectral data recorded with wavelength scans of the Designer Collagens showed a typical triple helical structure (FIGS. 2B-2J). Circular Dichroism scans were recorded at 220 nm with a temperature slope of 10 degrees Celsius per hour. This data demonstrated that the Designer Collagens maintain a triple helical structure at a temperature close to normal human body temperature (FIGS. 2K-2S).

EXAMPLE 6

Integrins Interact with Designer Collagens Containing GLPGER, GLPGEN, GLPGEK, GRPGER, GRPGEN, GRPGEK, GFPGER, GFPGEN, and GFPGEK Cell-binding Inserts Binding of recombinant forms of integrins α1 and α2 I domains to immobilized Designer Collagens with GLPGER, GLPGEN, GLPGEK, GRPGER, GRPGEN, GRPGEK, GFPGER, GFPGEN, and GFPGEK, motifs were determined by ELISA-based assays (FIGS. 3A-3B and FIGS. 4A-4B). Binding of recombinant forms of integrins α1 and α2 I domains to immobilized Designer Collagens with GRPGER, GLPGER, and GFPGER, was determined by Surface Plasmon Resonance analysis (FIGS. 5C and 5D-5F). The Designer Collagens with GLPGER, GRPGER, and GFPGER support the binding of α1 and α2 I domains (FIGS. 4A-4B, grey bars) via a metal ion dependent manner since binding is completely abolished by EDTA (FIGS. 4A-4B, white bars). C2C12 cells stably expressing either integrin α1 or α2 subunit (C2C12-α1 or C2C12-α2) were used to determine whether the Designer Collagens with GLPGER, GRPGER, and GFPGER motifs support adhesion of these cell lines.

Figure 5A:
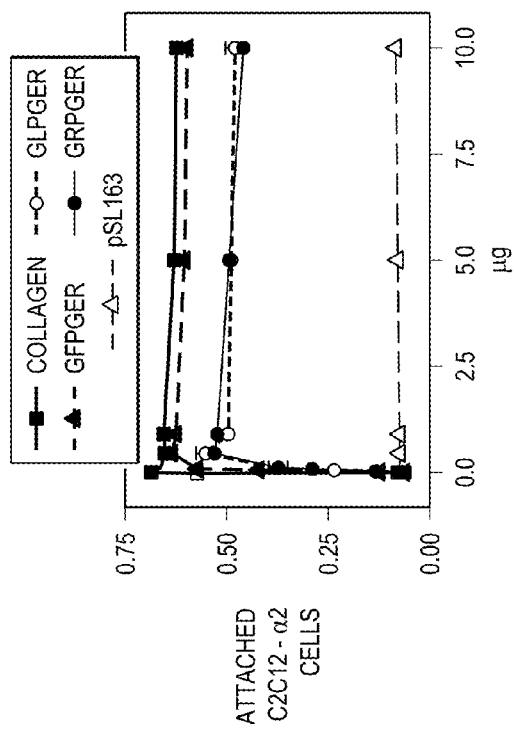
Figure 5B:
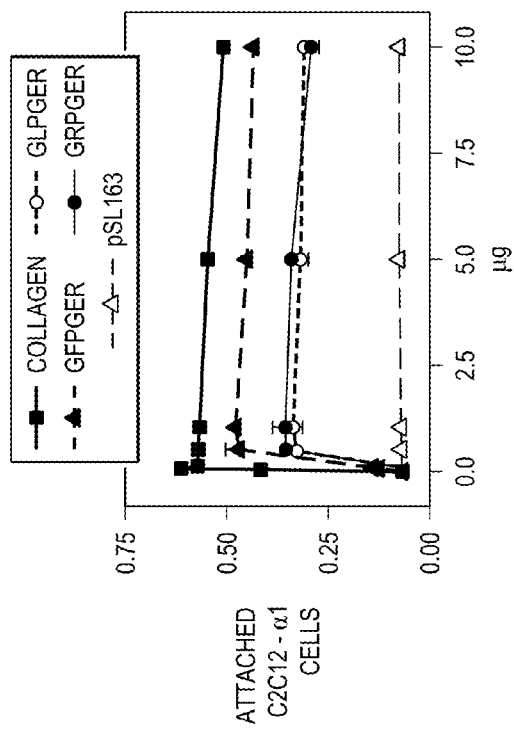
Figure 5C:
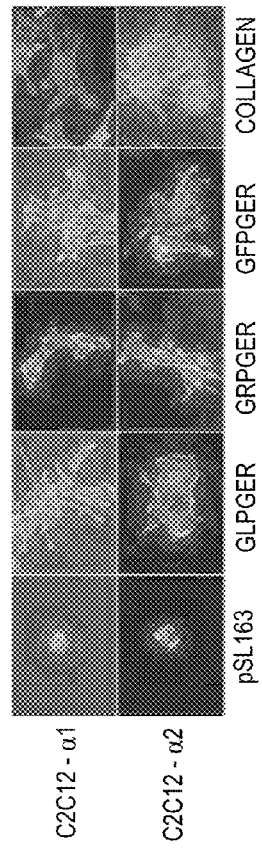

As shown in FIG. 5A, the Designer Collagens allowed adherence of C2C12-α1 cells or C2C12-α2 cells at a similar level of adherence to collagen type I, a positive control. Because pSL163 is a Designer Collagen without an 'inserted' motif, it is used as a negative control and did not mediate adherence of either cell type. This is an invaluable control because it implicates specific sequences are responsible for the interactions and not solely the presence of a triple helical protein. C2C12 parental cells did not adhere on any substrates; indicating the adhesion of C2C12-α1 and C2C12-α2 cells to the Designer Collagens is mediated by integrin α1β1 and α2β1. Cell adherence to substrates via specific integrins will exhibit outside-in signaling to induce intracellular signaling pathways, which will manifest as a morphology change resulting in spreading of cells. Adhered C2C12-α1 and C2C12-α2 cells on the Designer Collagens exhibited spreading within 60 minutes incubation at 37° C. in the presence of 5% $CO_2$ (FIG. 5B). This indicates that integrin binding motifs, GLPGER, GRPGER, and GFPGER actively bind to cells and induce intracellular signaling pathways. In addition, the Designer Collagens allow attachment and spreading of different cell types including endothelial cells in a dose-dependant manner (FIG. 5C), fibroblasts (MRC5), smooth muscle cells, and chondrocytic cells (SW1353) (FIGS. 5D-5F).

EXAMPLE 7

Designer Collagens with GLPGER, GRPGER, and GFPGER Motifs are Non-thrombogenic

The Designer Collagens support adherence of different cell types, some through an interaction with α2β1. Thus, whether Designer Collagens activated platelets by binding to integrin α2β1 was examined. FIG. 6 shows that Designer Collagens did not induce platelet aggregations at a 10-fold higher concentration than collagen type I, which aggregates platelets to over 90% in 10 minutes.

EXAMPLE 8

Designer Collagen with an Inserted Motif of GFPGEN Selectively Binds to Integrin α1β1, but not to α2β1

Figure 7C:
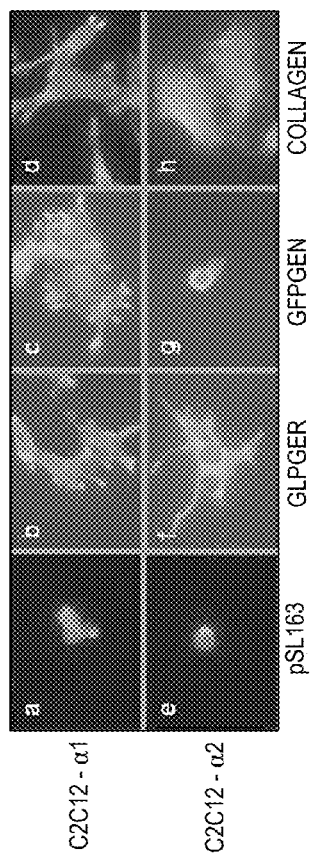
Figure 7D:
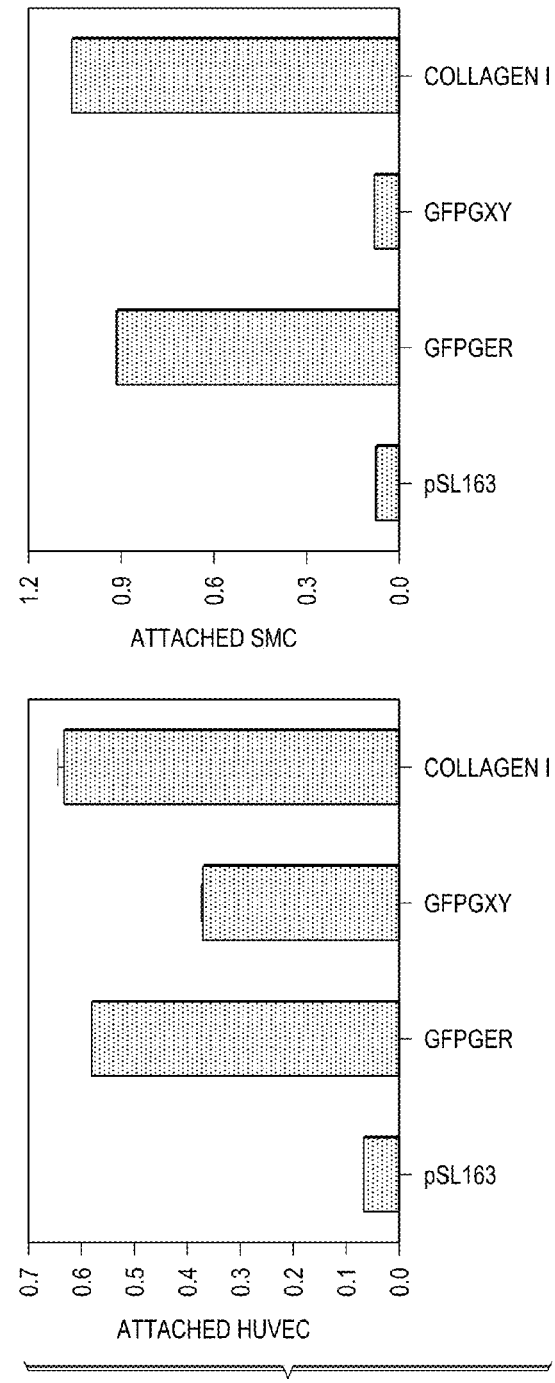

The Designer Collagen with a GFPGEN motif was expressed in *E. coli* and purified. It was tested for binding to integrin α1 and α2 I domains by ELISA based assays and Surface Plasmon Resonance analysis. The integrin α1 I domain binds to immobilized GFPGEN containing Designer Collagen, while the integrin α2 I domain fails to bind to Designer Collagen containing GFPGEN motifs (FIG. 7A). Integrin α1 and α2 I domains bind to immobilized GFPGER containing Designer Collagen and collagen type I as shown previously. In cell adherence assays, C2C12-α1 cells only adhere on GFPGEN containing Designer Collagen, but C2C12-α2 cells and C2C12 parental cells do not (FIG. 7B), this indicates that GFPGEN selectively interacts with integrin α1β1. The interaction of integrin α1β1 with GFPGEN induces intracellular signaling as shown by spreading of C2C12-α1 cells on a GFPGEN containing Designer Collagen (FIG. 7C). GFPGEN containing Designer Collagen also supported adhesion and spreading of human endothelial cells (FIG. 7D, where GFPGXY is GFPGEN, HUVEC graph). GFPGEN containing Designer Collagen did not support the adherence of smooth muscle cells (SMC) (FIG. 7D, where GFPGXY is GFPGEN, SMC graph). Integrin α2β1 is expressed on endothelial cells as well as smooth muscle cells.

Intracellular pathways activated upon cell adherence to Designer Collagens with inserted motifs of GFPGER and GFPGEN were determined herein. Activation of focal adhesion kinase (FAK) was detected in human dermal microvascular endothelial cells lysate 30 minutes after adherence to Designer Collagens and Collagen type1, but not P163 as demonstrated by Western blot analysis (FIGS. 8A-8F). Binding and oligomerization of both α1 and α2 in complex with α1 leads to autophosphorylation of Y397. Therefore, the results demonstrated by activation of FAK pY397 by Collagen type 1 and Designer Collagens show Designer Collagen not only bind to integrins, but mediate intracellular signaling. Collagen type 1 will preferentially bind α2 when both ligands are available. α2 signaling does not activate Shc, however it activates p38. Results herein indicate a strong activation of Shc by GFPGEN containing Designer Collagen, an activation of Shc by GFPGER containing Designer Collagen, and minimal to no activation of Shc by Collagen type 1. The results also indicate a strong activation of p38 by Collagen type 1, activation of p38 by GFPGER containing Designer Collagen, and minimal to no activation by GFPGEN containing Designer Collagen.

The data shown indicates reproducible and predictable activation signals by Collagen type 1. However, GFPGER containing Designer Collagen despite the capability of binding both α1 and α2 does not activate Shc or p38 in the same manner as Collagen type 1. These data suggest a more equal preference of GFPGER containing Designer Collagen to bind α1 and α2 when compared to Collagen type 1. These intracellular signaling properties add to the usefulness of Designer Collagens mediating specific cell functions such as angiogenesis, wound healing, adhesion prevention, cell recruitment, cell proliferation, and cell death.

EXAMPLE 9

Designer Collagen with a GFPGEN Motif is Non-thrombogenic

The Designer Collagen with a GFPGEN motif is non-thrombogenic as shown in platelet aggregation assays (FIG. 6). Since GFPGEN only binds to integrin α1β1, while GFPGER binds to both integrin α1β1 and α2β1, whether GFPGER and GFPGEN could inhibit collagen-induced platelet aggregations was examined. GFPGER shows inhibitory effects on collagen type I induced platelet aggregation. This indicates that the Designer Collagen binds to integrin α2β1 on platelets without activation and competitively blocks the binding of native collagen type I (FIG. 9). GFP-GEN containing Designer Collagen did not inhibit collagen induced platelet aggregation, indicating that GFPGEN does not compete with native collagen type I for the binding to integrin α2β1 on platelets. It is known that integrin α1β1 is not expressed on platelets.

EXAMPLE 10

Figure 10A:
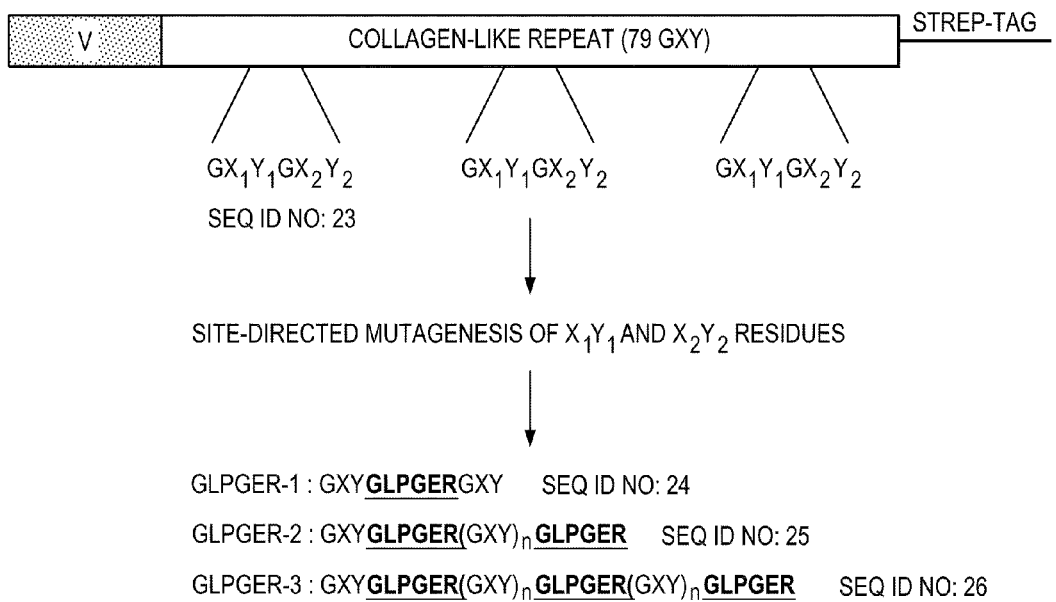
FIG. 10F shows GLPGER(4) and GLPGER (5), where GLPGER(4) and GLPGER(5) contain 4 and 5 repeats of the integrin binding sequence, GLPGER, respectively, bind α1 I domain with increased affinity in comparison to a single GLPGER repeat.
Figure 10B:
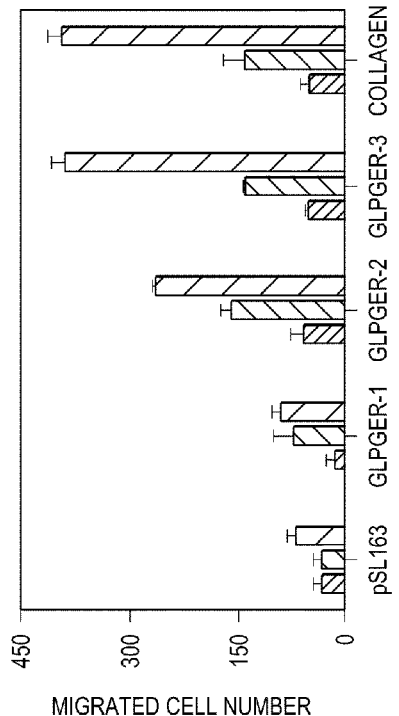

Cell Adhesion and Migration is Modulated by Density and Affinity of Integrin Specific Motifs on the Designer Collagen Substrates Whether modulation of density and affinity of integrin specific motifs on the Designer Collagen would influence cell behavior including attachment and migration on the substrates was determined. To this end, P163 was used to present spatial multiple integrin binding repeats that contain one, two, three, four or five repeats of GLPGER sequences. GXY repeat sequences are located between the GLPGER repeats to provide space between the integrin specific motifs (GLPGER-1, GLPGER-2, and GLPGER-3) (FIG. 10A). The Designer Collagens form oligomers on a polyacrylamide gel under non-reducing condition and also exhibited a typical triple helix structure with melting temperature values of 36.5° C. in thermal transition analyzed by CD spectroscopy. Surface Plasmon Resonance analysis was performed by passing over I domains to immobilized GLPGER-1, GLPGER-2, and GLPGER-3. The results indicated that α1 I and α2 I domains bound to the Designer Collagens in the presence of 1 mM $MgCl_2$ (FIG. 10B, where Y axis is α1 I domain and 11c, where Y axis is α2 I domain) and the binding was abolished in the presence of 1 mM EDTA. Normalized representative binding profiles of the I domains to captured GLPGER-1, GLPGER-2, and GLPGER-3 resulted in an increased in the binding affinity of the I domains to Designer Collagens with increased number of GLPGER repeats. The dissociation constant (KD) of integrin α1 I domain to captured GLGPER repeats was 1.33±0.15 μM, while that of integrin α2 I domain was 39.7, 25.9, and 11.8 μM to captured GLPGER-1, GLPGER-2, GLPGER-3, respectively.

Figure 10C:
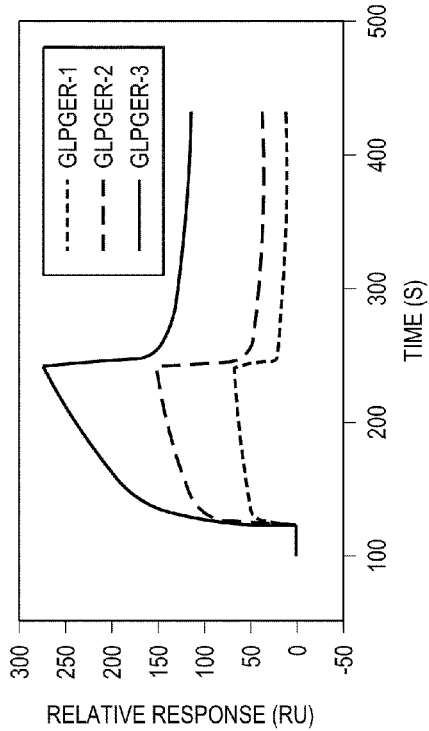
Figure 10D:
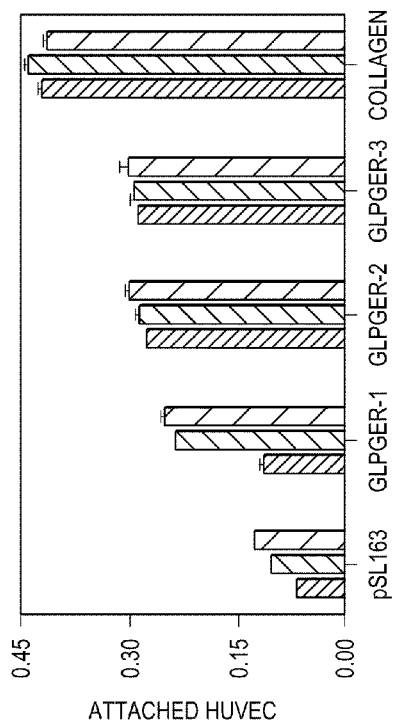

To assess the specificity of cell-substrate interactions, cell adhesion to the Designer Collagens was investigated by seeding human endothelial cells in serum-free medium containing 1 mM $MgCl_2$ and 1 mM $CaCl_2$ to 96 wells coated with increased concentration of GLPGER-1, GLPGER-2, GLPGER-3, Collagen type I, and P163. All GLPGER repeats served as a substrate for the attachment of the endothelial cells, as did type I Collagen (FIG. 10C). The attachment of cells depends on surface density of GLPGER contributed from amounts of coated substrates as well as numbers of integrin specific motifs, which give rise to increased attachment of the endothelial cells on the substrates.

Figure 10E:
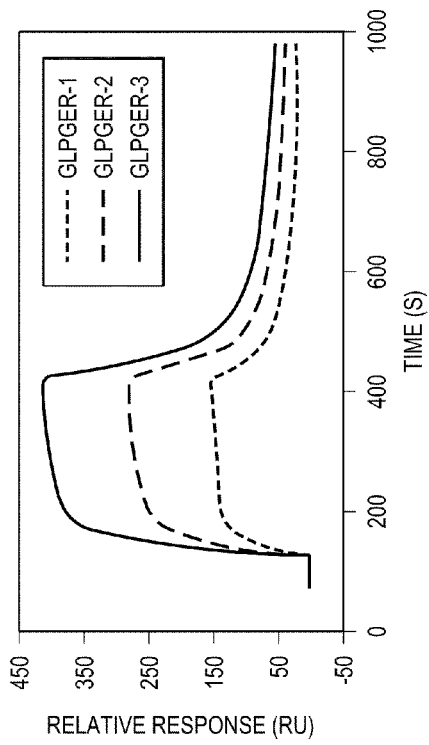
Figure 10F:
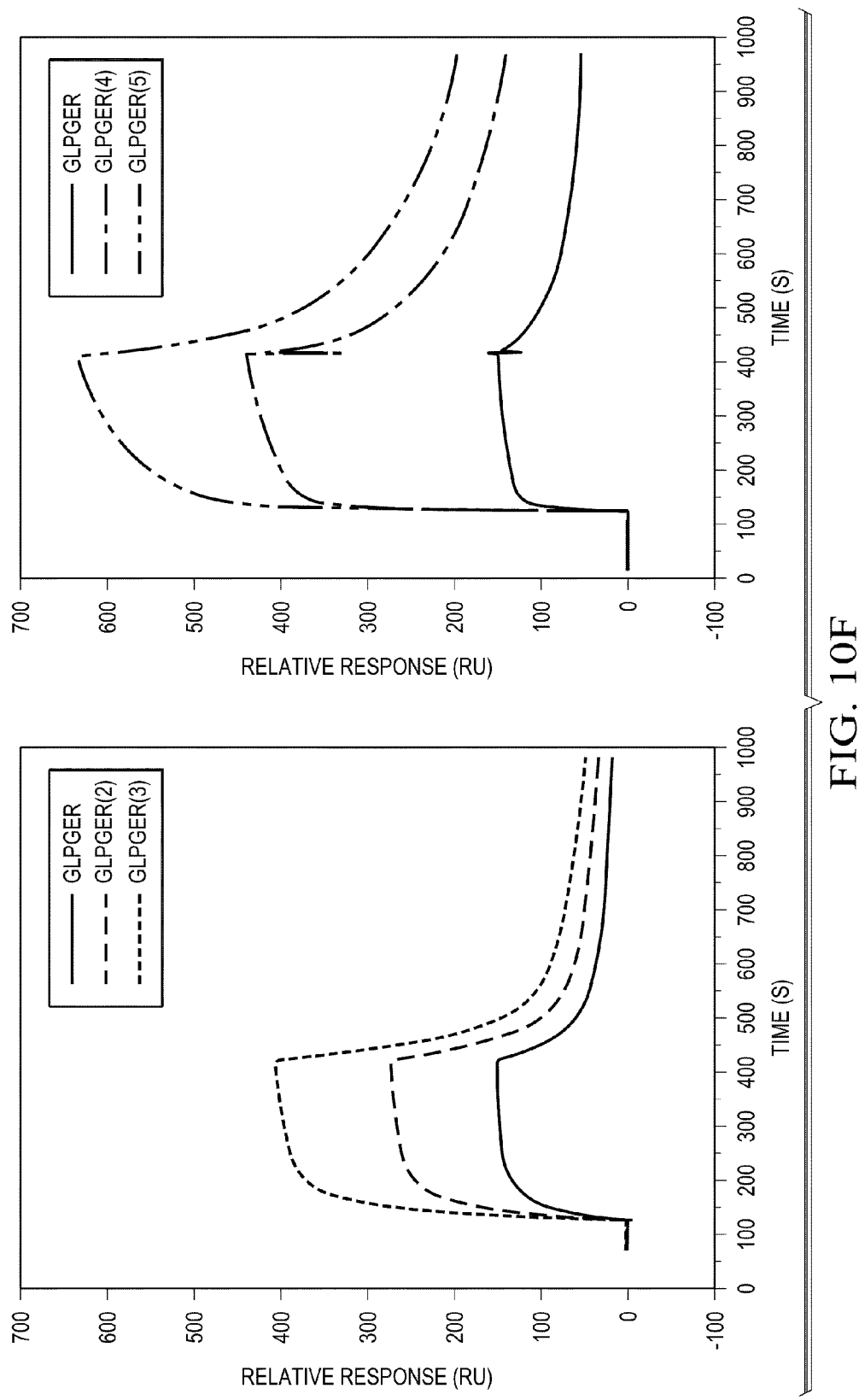

The effect of ligand density and affinity on endothelial cell migration was determined by counting migrated cells after a 4 hr time period in the presence and absence of soluble Designer Collagens GLPGER-1, GLPGER-2, GLPGER-3, and type I Collagen and P163. These results showed that the integrin specific motifs on Designer Collagens are able to support cell migration in the absence of other cell-substrate adhesive interactions. Increased density and numbers of integrin specific motifs on Designer Collagens resulted in a dramatic increasing of cell migration that reached the highest level in comparison to Collagen type I (FIG. 10E). The endothelial cell migration is enhanced in a dose-dependent manner and controlled by modulating ligand surface density and binding affinity. FIG. 10F shows that Designer Collagens containing 4 and 5 repeats of the integrin binding sequence, GLPGER, respectively, bind α1 I domain with increased affinity in comparison to a single GLPGER repeat.

Designer Collagen is prepared as a pathogen-free biomaterial using a prokaryotic expression system. Prokaryotic expression systems can be scaled up with current manufacturing process pipelines and offer lot-to-lot consistency with cost-effectiveness. Designer Collagens have the capacity to form a triple helix without the presence of hydroxyproline, which adds a cost advantage. Designer Collagens have multiple and different inserted sequences, which requires separate production. The mixing of Designer Collagens for product optimization is possible post-purification. A possible limitation of prokaryotic expression is the lack of post-translation modification. Certain applications of Designer Collagens do not require post-translational modification, but if the need arises, alternative expression systems could be used. Current methods of collagen purification rely on purification methods from an animal source. These methods are inconsistent, expensive, and offer only native collagen.

Designer Collagens that do not contain any 'inserted' residue such as, pSL163, showed minimal binding to integrin I domains did not support the adherence of different cell types. Thus, these Designer Collagens could be used as anti-adhesion biomaterials. Anti-adhesion materials currently use cellulose or other coatings of a mesh to prevent the formation of adhesion after trauma or surgery. Designer Collagens containing could be useful in cell recruitment or maintenance of a certain cell type in a localized area. The adherence to and subsequent intracellular signaling of α1β1 and α2β1 by GFPGER containing Designer Collagens could be useful in stimulating multi-step processes such as angiogenesis. Designer Collagens containing GFPGEN could be optimal vascular graft coatings or stent coatings. This unique biomaterial supports the adherence and spreading of endothelial cells but not smooth muscle cells and does not mediate platelet aggregation. Alternative formulations may include chimeric Designer Collagens encompassing different protein domains to achieve a desired function, chemical crosslinking effects needed to instill a certain property with regard to stability, a chemical effect needed to facilitate attachment of Designer Collagens to a certain material, and undetermined 'inserts' which impart a new property and function of Designer Collagens for new markets. These undetermined 'inserts' could range in function, however, other representative targets include bone sialoprotein binding sequences, integrins α10β1 and α11β1 binding sequences, and many extracellular matrix constituents.

EXAMPLE 11

Designer Collagen Conjugation to PEG Linker with Photoreactive Crosslinks

Figure 11:
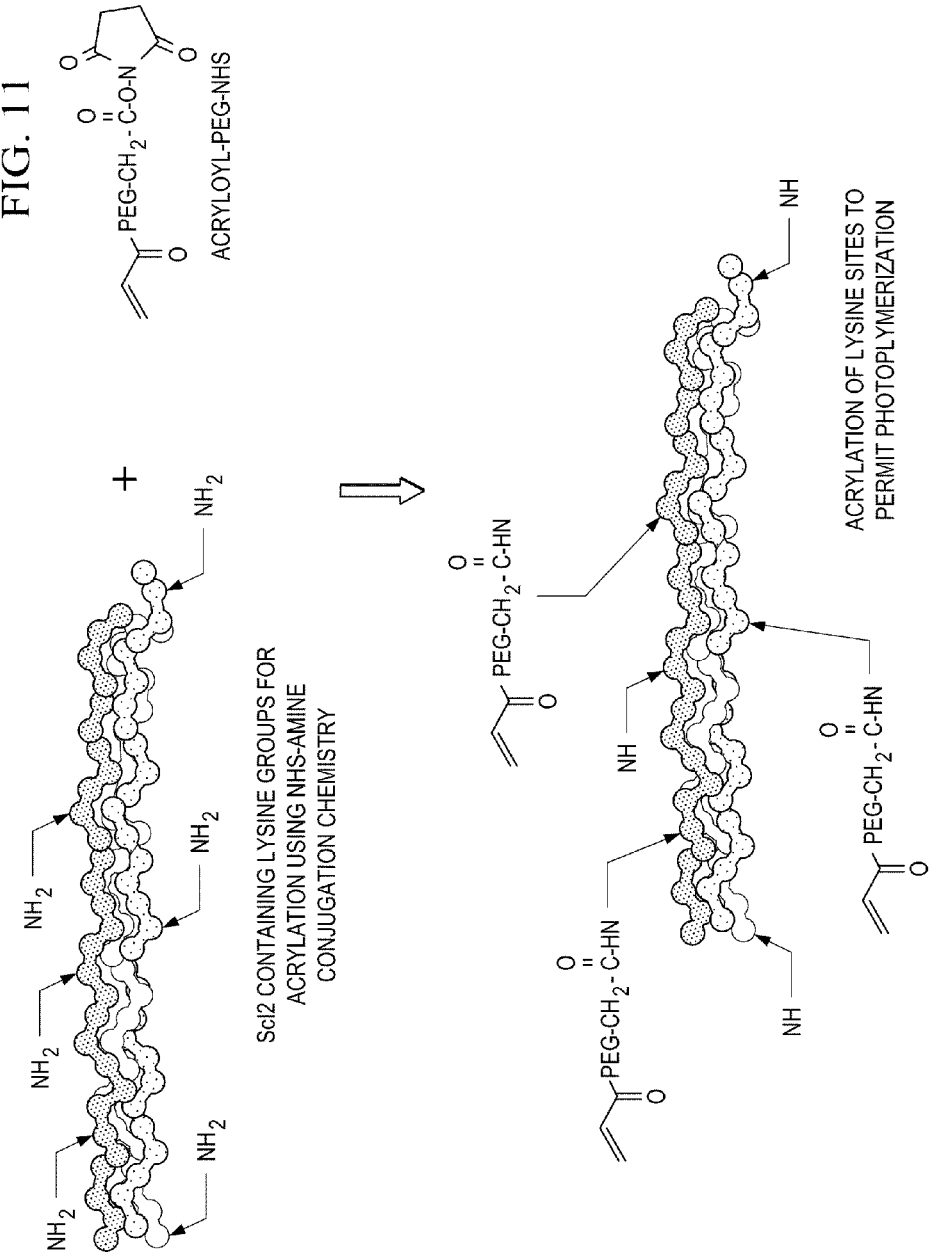
FIG. 11 shows the synthetic route of the functionalization of Designer Collagens (P163, GFPGER containing Designer Collagen, and GFPGEN containing Designer Collagen) with photoreactive crosslink sites to enable conjugation into PEGDA hydrogels.

Designer Collagens and a rat tail collagen I control (Sigma Aldrich) were functionalized with photoreactive crosslink sites to enable hydrogel formation. (FIG. 11). Designer Collagens contain ~9% lysine groups that readily facilitate bioconjugation chemistry via the established NHS-lysine ε-amino group reaction. Briefly, proteins were reacted with acrylate-PEG-N-Hydroxysuccinimide (Ac-PEG-NHS, $M_W$ 2000) in 50 mM sodium bicarbonate buffer (pH 8.5) at room temperature. A molar ratio of 2:1 Ac-PEG-NHS:NH2 was used and the reaction was allowed to proceed for 18 h at room temperature with shaking. Excess Ac-PEG-NHS and other reaction byproducts were removed via dialysis (MWCO=20, 000). Functionalization was confirmed with infrared (IR) spectroscopy and gel electrophoresis.

EXAMPLE 12

Characterization of Functionalized Designer Collagen Proteins

Functionalized Designer Collagens were characterized by electrophoresis, circular dichroism, and α1 I domain binding. SDS-PAGE analysis was used to determine multimer formation of 163-F, GFPGER-F, and GFPGEN-F (F denotes functionalized). Briefly, denatured proteins were incubated at 95° C. for 5 min in the presence of 0.1% SDS and 2% β-mercaptoethanol. Non-denatured samples were incubated in 5% glycerol and kept on ice prior to electrophoresis on 12% SDS-PAGE gels. Gels were stained with coomassie blue, and protein migration as it corresponds to size was determined using protein standards.

Circular dichroism spectra of protein samples in water were recorded on a Jasco J720 spectropolarimeter in a thermostatically controlled cuvette with a 0.5-mm path length. Data were collected in a wavelength range from 250 nm to 190 nm, and integrated for 1 s at 0.2-nm intervals with a bandwidth of 1 nm. For each spectrum, ten scans were averaged and the contribution from the buffer was subtracted. For thermal transition experiments, the ellipticity at 220 nm was monitored as the sample temperature was increased from 25 to 45° C., with an average temperature slope of 10° C./h. Each independently prepared batch of protein was analyzed.

An enzyme-linked immunosorbant assay (ELISA) was utilized to assess the specificity of recombinant α1 I domain binding to control and functionalized Designer Collagens. Microtiter wells were coated with 1 µg per well of P163-F, GFPGER-F, GFPGEN-F, or rat tail derived collagen type I (Cultrex R&D) in PBS containing 1 mM $MgCl_2$ or 1 mM EDTA overnight at 4° C. The samples were blocked with PBS containing 1% BSA (w/v) for 1 hr. Five µM α1 I-domains were added to the wells and incubated for 2 h at room temperature. A mouse monoclonal anti-his-HRP conjugate (Alpha Diagnostics) was used to detect bound I-domains. The absorbance at 450 nm was measured using a Thermomax plate reader (Molecular Devices Corp, Menlo Park, Calif.). Experiments were performed in triplicate.

EXAMPLE 13

Cell Adhesion to Functionalized Designer Collagens

To confirm that each Designer Collagen retained appropriate cell interactions following conjugation to PEG, the ability of five distinct cell populations to interact with the functionalized proteins was examined in 2D: 1) C2C12 cells, which do not natively express α1 and α2 subunits; 2) C2C12 cells modified to stably express human α1 subunits (C2C12-α1); (3) C2C12 cells modified to stably express human α2 subunits (C2C12-α2); 4) bovine aortic endothelial cells (ECs); and 5) rat aortic smooth muscle cells (SMCs). Mouse myoblast C2C12, C2C12-α1, and C2C12-α2 cells were provided by Dr. Donald Gullberg (University of Bergen) and maintained in DMEM with 10% FBS (Hyclone) supplemented with no antibiotic, 1 mg/ml geneticin (Invitrogen), or 10 µg/ml of puromycin (InvivoGen), respectively.

For cell adhesion studies, microtiter plates were coated with functionalized and unmodified P163, GFPGER, and GFPGEN. Microtiter wells were coated with 1 µg per well of P163, GFPGER, GFPGEN, or rat tail derived collagen type I (Cultrex R&D) in PBS overnight at 4° C. The Designer Collagen solutions were filter-sterilized using a 0.22 µm PDVF membrane (Millipore) prior to application to the microtiter plate. For each protein, 15 wells (3 wells per cell type examined) were coated. After blocking with PBS containing 1% BSA for 1 h, the wells were rinsed extensively with PBS and cells were seeded onto the coated surfaces at 6,000 cell/$cm^2$.

Prior to seeding, cells were adapted to serum free media (DMEM containing 1 mM $CaCl_2$ and 1 mM $MgCl_2$) for 3 h, after which cells were harvested by brief exposure to 0.125% trypsin (Mediatech) and resuspended in serum free media supplemented with 0.2% BSA. Following 3 h exposure to the coated surfaces at 37° C./5% $CO_2$, cells were fixed with 4% paraformaldehyde and stained with rhodamine phalloidin (Invitrogen) and SybrGreen (Invitrogen). Representative fluorescence images were obtained using a Zeiss Axiovert microscope. Rat tail collagen I coated wells served as positive controls.

Fluorescence images (3 images per sample, 3 samples per protein) of Sybr Green and rhodamine phalloidin stained cells seeded onto coated tissue culture plastic were utilized to quantify the extent of cell adhesion and spreading. The number of cell nuclei per image was used as a quantitative assessment of cell adhesion on each test surface and was assessed by two independent observers. Since different cell seeding densities were employed for various cell types, these cell counts were then normalized to the observed average cell count on the corresponding collagen controls to permit comparison across cell types.

Average cell spreading, or cell area, was quantified by applying the Photoshop "magic wand" tool to the image background and adjusting the tool tolerance so that all extracellular regions were selected. The histogram function was then utilized to evaluate the extracellular pixels. The average pixels per cell ($A_{cell}$) for that image was then quantified as follows: $A_{cell}$=(total image pixels−extracellular pixels)/(total image nuclei). Pixels were then converted to microns using known objective scaling. Data are reported as mean±standard error of the mean, p<0.05.

EXAMPLE 14

Preparation of Biologically Active Peg-Designer Collagen Hydrogels

PEGDA was synthesized by adding acryloyl chloride dropwise to a solution of PEG (3.4 kDa) and triethylamine in anhydrous dichloromethane (DCM) under an argon blanket. The molar ratio of diester, acryloyl chloride, and triethylamine was 1:2.5:2.1, respectively. The reaction was maintained at low temperature to reduce undesired side reactions utilizing a salt/ice bath. After the addition of acryloyl chloride, the reaction was stirred overnight. The resulting solution was washed with 2M $K_2CO_3$ to remove acidic byproducts. The DCM phase was subsequently dried with anhydrous $MgSO_4$, and the PEGDA product was then precipitated in diethyl ether, filtered, and dried under vacuum. PEG functionalization was confirmed with IR and NMR spectroscopy. An ester peak at 1704 $cm^{-1}$ and loss of the hydroxyl peak at 3300 $cm^{-1}$ in the IR spectra of PEGDA was indicative of successful acrylation and 1H NMR confirmed an acrylation of ~85%.

Functionalized Designer Collagens were conjugated within PEGDA hydrogels to examine the retention of their specific bioactivities (in terms of cell adhesion) upon incorporation into 3D networks. Proteins were dissolved at 6 mg protein/mL in 20 mM acetic acid. PEGDA powder was then added to each solution to 5 wt %, followed by the addition of 10 µL/mL of a 300 mg/ml solution of UV photoinitiator 2,2-dimethoxy-2-phenyl-acetophenone in N-vinylpyrrolidone. The resulting solutions were sterile-filtered, pipetted between glass plates separated by 200 μm spacers, and polymerized by 10 min exposure to longwave UV light (~6 mW/cm$^2$, Spectroline). The resulting hydrogels were then immersed in PBS for 24 h. C2C12, C2C12-α1, C2C12-α2, EC, and SMC were harvested, resuspended in media containing 10% FBS, and seeded onto the swollen Designer Collagen-containing gels at 6,000 cell/cm$^2$. After 3 hours at 37° C./5% $CO_2$, cells were fixed with paraformaldehyde and stained with rhodamine phalloidin and SybrGreen. Representative fluorescence images were obtained using a Zeiss Axiovert microscope. Rat tail collagen I-containing hydrogels served as positive controls.

3 images per sample per protein of SybrGreen and rhodamine phalloidin stained cells seeded onta PEGDA hydrogels were utilized to quantify the extent of cell adhesion and spreading. The number of cell nuclei per image was used as a quantitative assessment of cell adhesion on each test surface and was assessed by two independent observers. Average cell spreading, or cell area, was quantified by applying the Photoshop "magic wand" tool to the image background and adjusting the tool tolerance so that all extracellular regions were selected. The histogram function was then utilized to evaluate the extracellular pixels. The average pixels per cell ($A_{cell}$) for that image was then quantified as follows: $A_{cell}$=(total image pixels−extracellular pixels)/(total image nuclei). Pixels were then converted to microns using known objective scaling. Data are reported as mean±standard error of the mean, $p<0.05$.

The utility of Designer Collagens was demonstrated in vascular applications by functionalizing Designer Collagens to permit their conjugation into PEGDA hydrogel networks. The ability to functionalize Designer Collagens without disrupting the native conformation, integrin binding affinity, and cell interactions of Designer Collagens was shown.

EXAMPLE 15

Confirmation of Designer Collagens Functionalization

Figure 12:
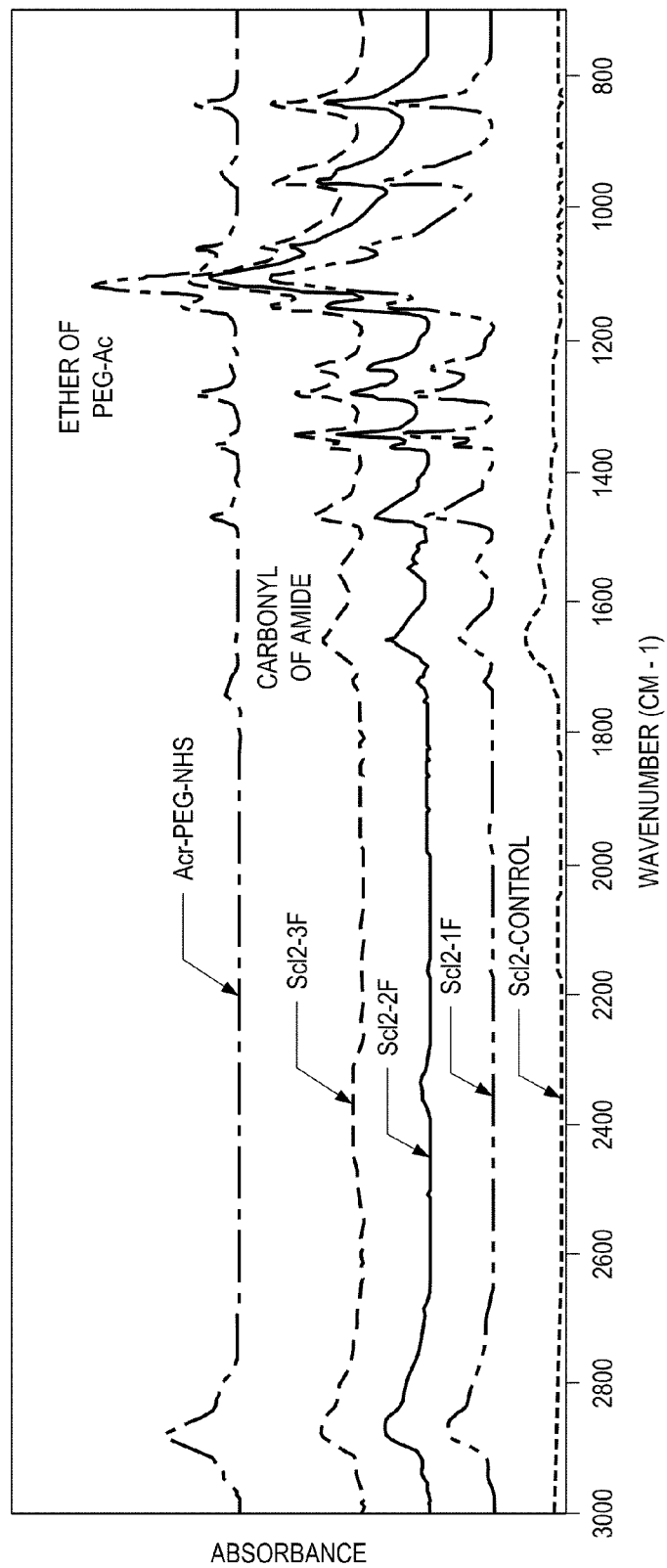
FIG. 12 shows the infrared spectra of functionalized Designer Collagens confirming conjugation of Designer Collagens with PEG-Ac linker.
Figure 13A:
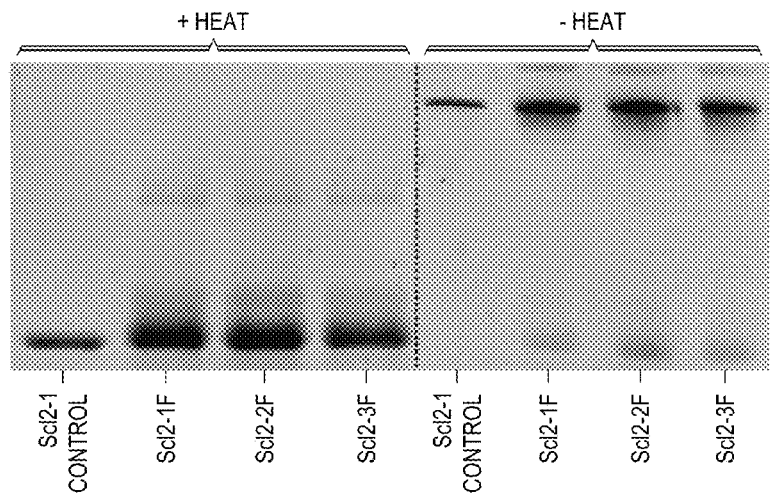
FIGS. 13A-13C show that functionalized Designer Collagens retained their triple helical conformation and biological activity.

The functionalized proteins, denoted —F, were first analyzed using IR spectroscopy. IR absorbance peaks assigned to the peptide (amide, C=O) at 1630 cm$^{-1}$ and PEG (ether, C—O—C) at 1110 cm$^{-1}$ were both present in the purified product, (FIG. 12). Control experiments confirmed that non-bonded PEG was removed by dialysis over the selected time period; thus, the presence of PEG in the product was concluded to be coupled to the Designer Collagens and collagen control. The ratio of the peak amide- to-peak ether absorbance was used to standardize the level of functionalization for each batch. As an additional confirmation of functionalization, collagen and Designer Collagens exposed to Ac-PEG-NHS were heat denatured and run on a native SDS-PAGE gel. The smeared bands associated with the products as compared to the unmodified controls confirmed conjugation and gave insight into polydispersity (FIG. 13A). Reduced electrophoretic mobility was attributed to increased molecular weight upon conjugation to the photoreactive PEG linker.

EXAMPLE 16

Maintenance of Triple Helical Structure and Bioactivity Following PEGylation

Figure 13B:
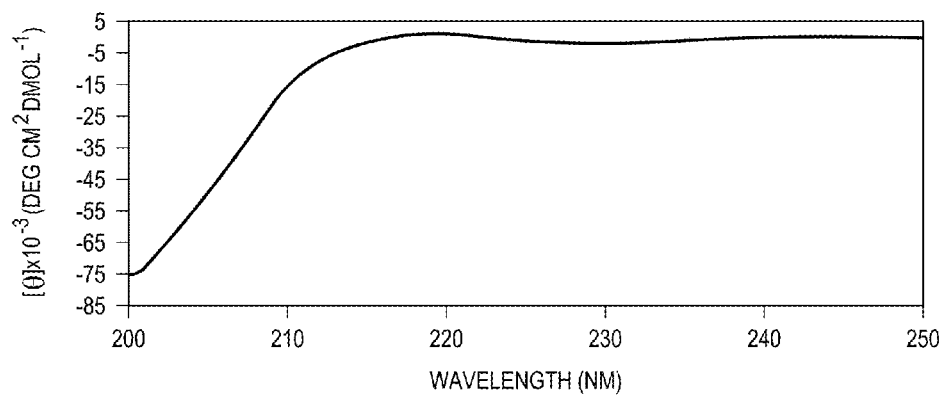
Figure 13C:
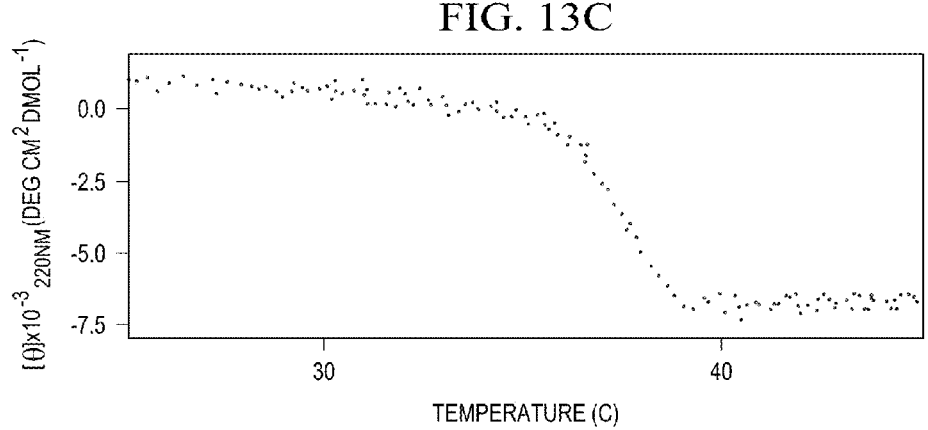

Extensive protein functionalization can disrupt protein conformation and adhesion site availability. It was therefore important to confirm that Designer Collagens retained their triple helical conformation and biological activity. Designer Collagens ran as homogeneous trimers, with an estimated molecular weight of ~120 kDa, under non-denaturing electrophoretic conditions, in comparison to their heat-denatured counterparts, which exhibited molecular masses of ~35 kDa (FIG. 13A). Retention of a triple helical conformation by Designer Collagens-F was assessed by circular dichroism. P163-F spectra were analyzed and exhibited peaks at 220 nm indicating the presence of a triple helical structure (FIG. 13B). The thermal stability of P163-F triple helices was also monitored, and observed thermal transitions were similar for both P163 and P163-F proteins (FIG. 13C).

Figure 14:
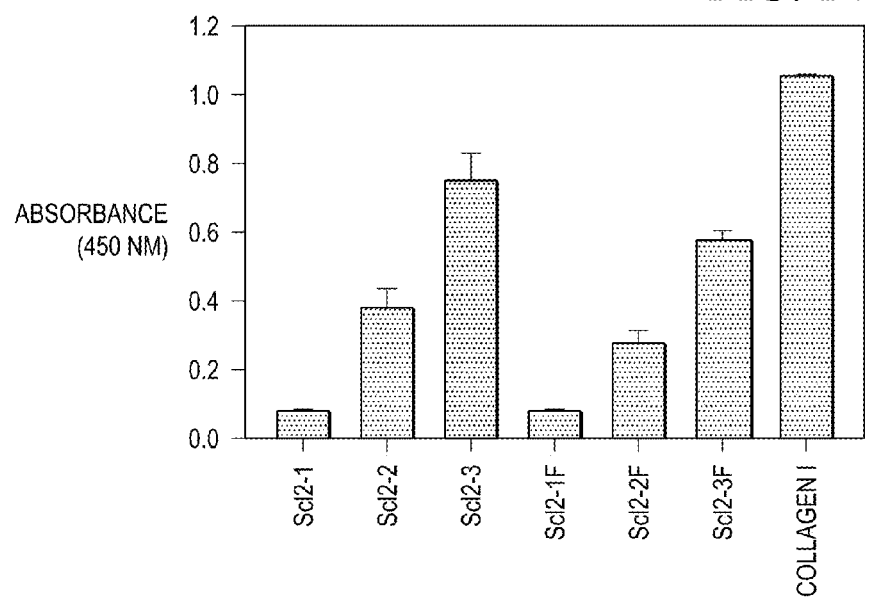
FIG. 14 shows microtiter plates were coated with Designer Collagens and functionalized Designer Collagens at a concentration of 1 mg/well. Recombinant α1 I-domains (5 μM) were allowed to adhere for 2 h and ELISA was performed to quantify integrin binding.

Retention of expected bioactivity was qualitatively evaluated by solid phase binding assays. Microtiter wells were coated with unmodified P163, GFPGER, GFPGEN, P163-F, GFPGER-F, GFPGEN-F or collagen type I and exposed to recombinant human α1 I-domains. As expected, P163 bound minimal α1 I domains levels and collagen type I bound maximal α11 levels (FIG. 14). Furthermore, GFPGER and GFPGEN bound α1 I-domain at levels intermediate between collagen I and P163. Similar trends were observed with functionalized Designer Collagens, which indicated that appropriate integrin binding was retained on functionalization.

EXAMPLE 17

Cell Adhesion to Functionalized Designer Collagens

Figure 15A:
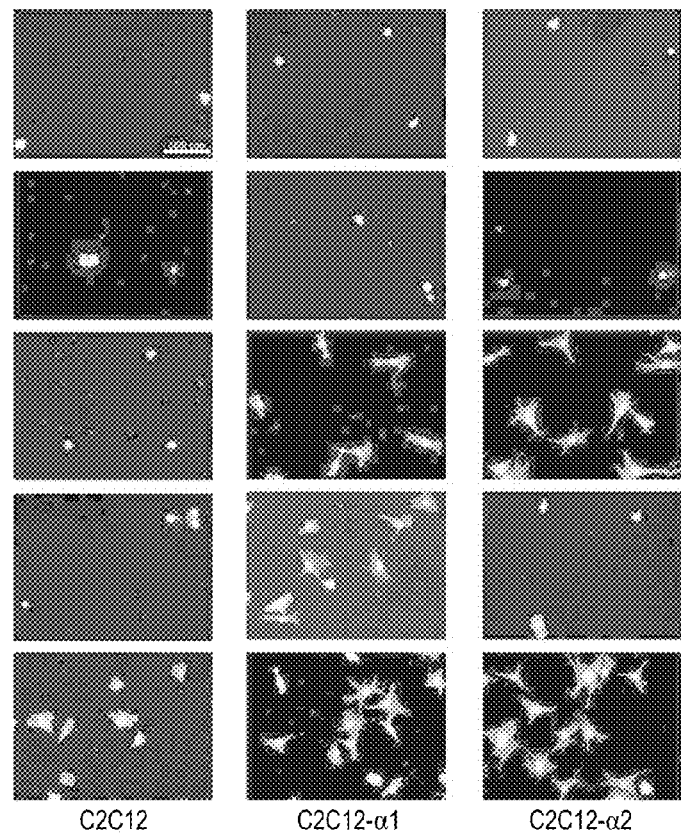
FIG. 15A shows that high binding polystyrene 96 well plates were coated with BSA, P163-F, GFPGER-F, GFPGEN-F, and functionalized type I collagen (collagen-F) at 1 μg protein per well. C2C12, C2C12-α1, C2C12-α2 cells were seeded at a density of 6000 cell/cm$^2$ and allowed to spread for 3 h. Attached cells were fixed with 4% paraformaldehyde, stained with rhodamine phalloidin (for F-actin) and SybrGreen (nucleus), and imaged by fluorescence microscopy. Scale bar applies to all images and equals 100 μm.
Figure 15B:
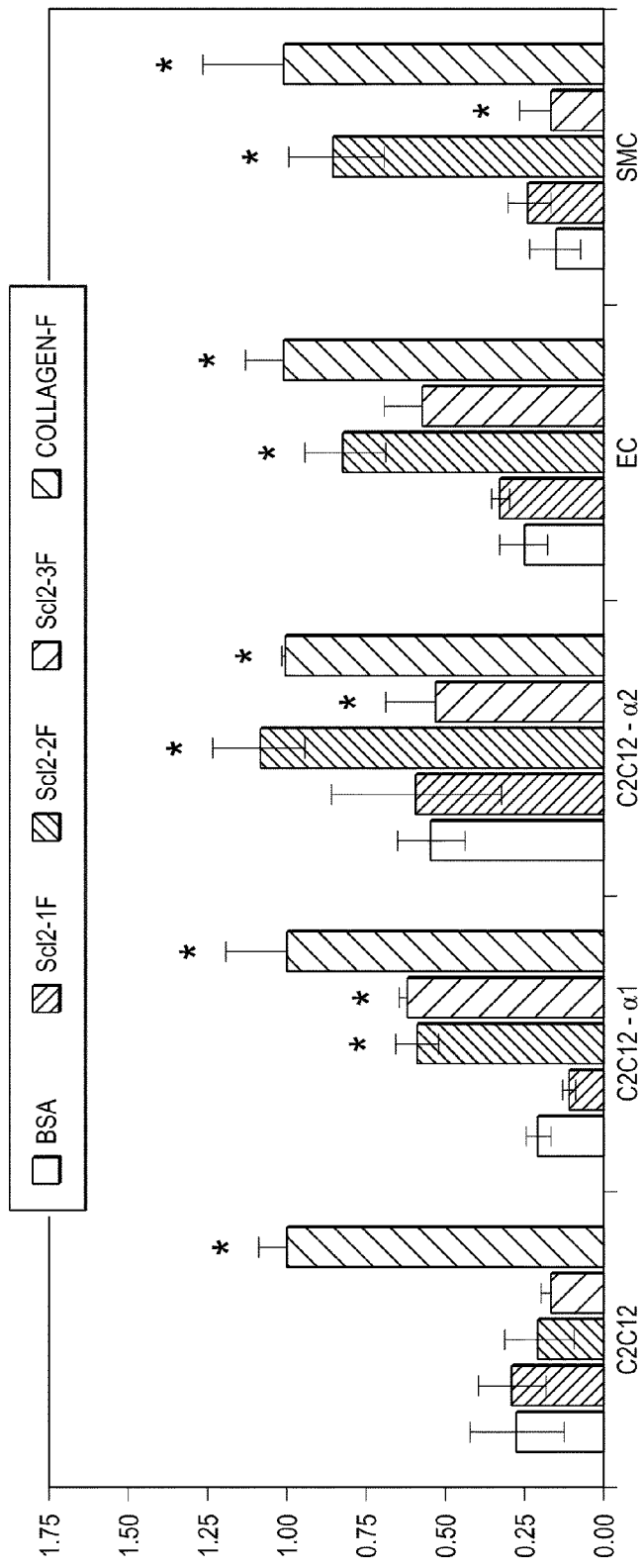
FIG. 15B shows relative cell adhesion on Scl2-F versus collagen-coated tissue culture polystyrene. *, indicates a statistically significant different with the corresponding BSA control, $p<0.05$.

To confirm that cells could recognize and bind the integrin binding motifs in Designer Collagen-F proteins, cell adhesion and spreading studies were performed using mouse C2C12 cells that were modified to express human integrin α1 subunit, C2C12-α1, or human integrin α2 subunit, C2C12-α2. The expression of α1 or α2, and α1 subunits on the cell surface of the cells was confirmed by immunocytochemistry prior to cell culture studies. C2C12, C2C12-α1, or C2C12-α2 were allowed to adhere and spread for 3 h on microtiter plates coated with 1 μg protein per well. GFPGER-F and GFPGEN-F induced spreading of C2C12-α1 (FIG. 15A, second column), as did the collagen-F positive control. However, C2C12-α2 cells (FIG. 15A, third column), adhered and spread on GFPGER-F and collagen-F but not on GFPGEN-F. These results were consistent with the known integrin binding of each protein. As expected, P163-F coated surfaces displayed similar cell adhesion and spreading as BSA-coated negative controls. FIG. 15B shows that these qualitative assessments were further underscored by quantitative analysis of cell adhesion (BSA, used here as a negative control; Scl2-1F, also referred to as P163-F; Scl2-2F, also referred to as GFPGER-F; Scl2-3F, also referred to as GFPGEN-F, Collagen-F, type I collagen used as a positive control).

Figure 16A:
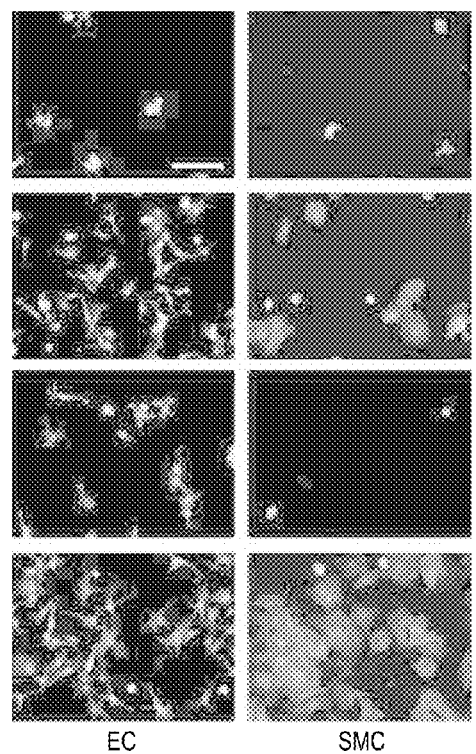
FIG. 16A shows that high binding polystyrene 96 well plates were coated with P163-F, GFPGER-F, GFPGEN-F, and functionalized type I collagen (collagen-F) at 1 μg protein per well. ECs and SMCs were seeded at a density of 6000 cell/cm$^2$ and allowed to spread for 3 hours. Attached cells were fixed with 4% paraformaldehyde, stained with rhodamine phalloidin and SybrGreen, and imaged by fluorescence microscopy. Scale bar applies to all images and equals 100 μm.
Figure 16B:
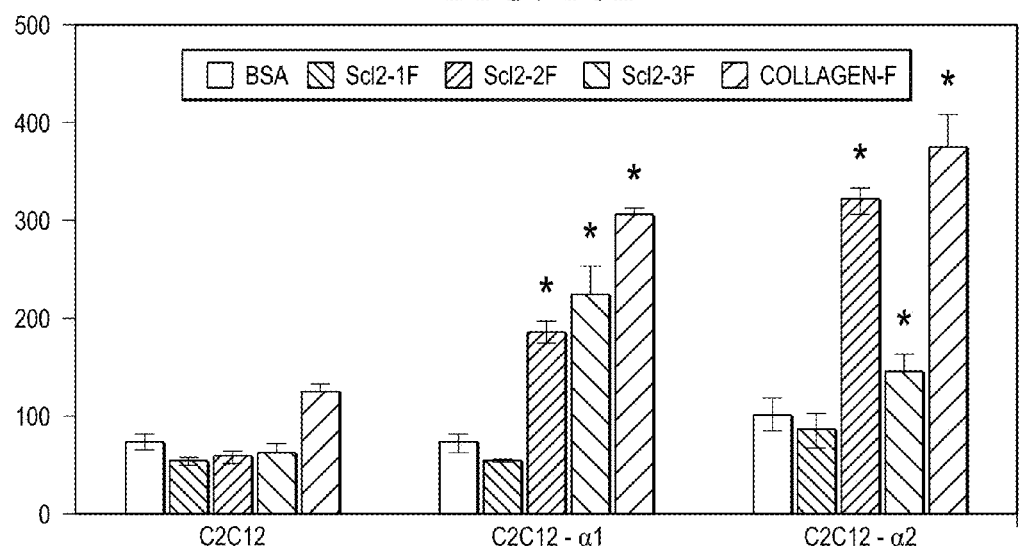
FIG. 16B shows relative cell spreading on Scl2-F versus collagen-coated tissue culture polystyrene. *, indicates a statistically significant different with the corresponding BSA control, $p<0.05$.

FIG. 16A shows the utility of functionalized Designer Collagens in vascular applications, the attachment and spreading of endothelial cells and smooth muscle cells. Both smooth muscle cells and endothelial cells strongly spread on collagen-F coated surfaces. Furthermore, GFPGER-F and GFPGEN-F coated surfaces mediated endothelial cell attachment and spreading, although endothelial cells adhesion on P163-F coated wells was minimal. As with endothelial cells, smooth muscle cells were unable to significantly attach to P163-F. However, in contrast to endothelial cells, smooth muscle cells were able to spread on GFPGER-F coated surfaces but not on GFPGEN-F coated wells. Therefore, GFPGER-F and GFPGEN-F promoted selective attachment and spreading of endothelial cells versus smooth muscle cells. FIG. 16B shows that these qualitative assessments were further underscored by quantitative analysis of cell spreading (BSA, used here as a negative control; Scl2-1F, also referred to as P163-F; Scl2-

2F, also referred to as GFPGER-F; Scl2-3F, also referred to as GFPGEN-F, Collagen-F, type I collagen used as a positive control).

EXAMPLE 18

Bioactive Hydrogels with Cell-specific Adhesion

Functionalized Designer Collagens were conjugated within 5 wt % PEGDA hydrogels to examine the retention of their specific bioactivities in terms of cell adhesion upon incorporation into 3D networks. PEGDA was selected as the base-material for the hydrogel network due to its established non-thrombogenicity, making these gels particularly desirable for vascular applications. However, the biological blank slate character of PEGDA also allowed observed cell binding to Designer Collagens containing gels to be attributed to the presence of the inserted 'biologically active sequence' alone.

Figure 17A:
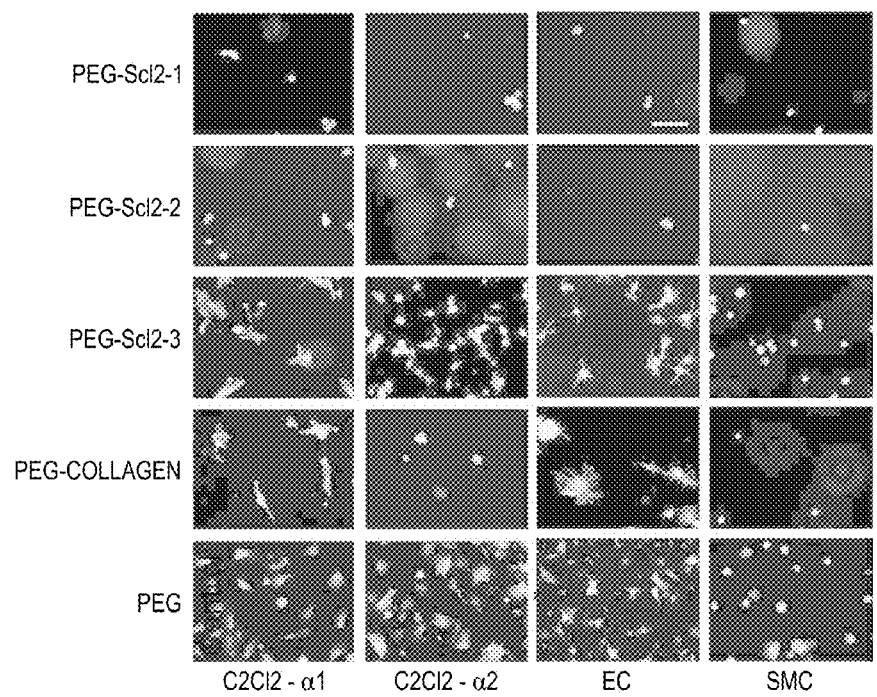
FIG. 17A shows that PEG-Designer Collagen hydrogels were fabricated by combining 5 wt % PEGDA (3.4 kDa) with photoinitiator (Irgacure 2959), 6 mg protein/mL of P163-F, GFPGER-F, GFPGEN-F, or functionalized type I collagen. PEG hydrogels served as a negative control. Cells were seeded at a density of 6000 cell/cm$^2$ and allowed to spread for 3 hours. Attached cells were fixed with 4% paraformaldehyde, stained with rhodamine phalloidin and SybrGreen, and imaged by fluorescence microscopy. Scale bar applies to all images and equals 100 μm.
Figure 17B:
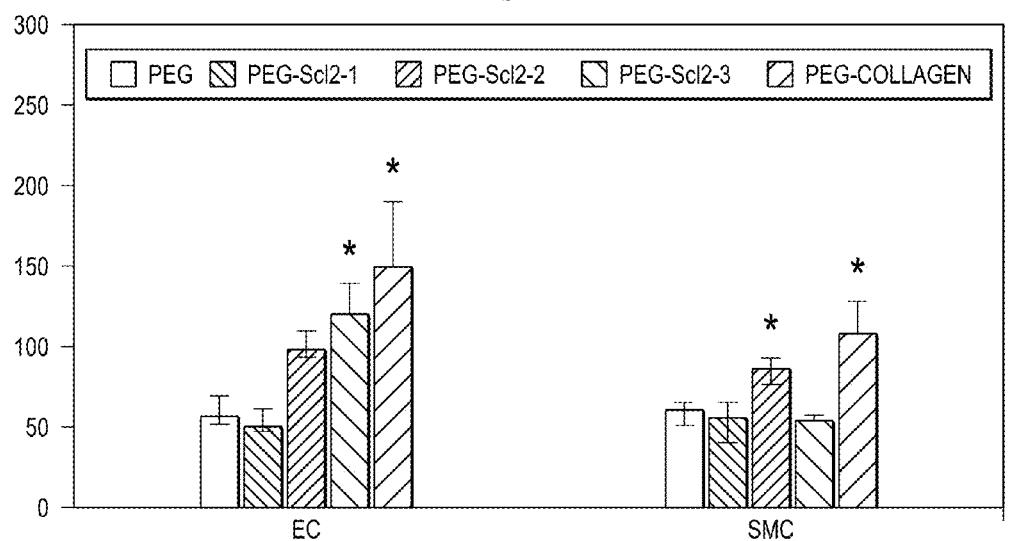
FIG. 17B shows relative cell spreading on PEG-Scl2 gels versus PEG-Collagen gels. *, indicates a statistically significant different with the corresponding PEG control, $p<0.05$.

Cell adhesion and spreading on the Designer Collagen-based hydrogels was examined using the C2C12-$\alpha$1, C2C12-$\alpha$2, endothelial cells, and SMCs, FIG. 17A. As anticipated, each cell type spread on collagen-F coated surfaces, although the extent of their spreading on the gel surfaces was significantly lower than on the collagen-F coated polystyrene well. This observation is consistent with studies demonstrating a reduction in cell spreading with decreasing substrate stiffness. Similarly, GFPGER-F promoted adhesion of C2C12-$\alpha$1, C2C12-$\alpha$2, endothelial cells, and SMCs. GFPGEN-F gels, however, were unable to support C2C12-$\alpha$2 and SMC adhesion, as can be seen by comparison with P163-F gels and PEGDA negative controls. FIG. 17B shows that these qualitative assessments were further underscored by quantitative analysis of cell spreading (BSA, used here as a negative control; PEG-Scl2-1, also referred to as P163-F gels; PEG-Scl2-2, also referred to as GFPGER-F gels; PEG-Scl2-3, also referred to as GFPGEN-F gels, PEG-Collagen, type I collagen used as a positive control). Thus, functionalized Designer Collagens can be incorporated into 3D matrices to generate cell selective, bioactive hydrogels.

Tissue engineered vascular graft clinical outcomes could be significantly improved by limiting two primary complications associated with vascular grafts, namely thrombosis initiated by platelet adhesion and hyperplastic ingrowth of smooth muscle cells. The ability to differentially bind specific cells is therefore critical to the tissue engineered vascular graft field, where endothelial cell attachment is needed to provide a bioactive blood-graft interface but attachment of blood cells and vessel wall cells is undesired. This is a challenging problem because most scaffolds promote cell attachment through a layer of adsorbed serum proteins that enable the non-selective adhesion of a range of cell types. In the current study, a novel biomaterial platform is disclosed that does not rely upon adsorbed proteins for cell adhesion and thus can be manipulated to promote selective cell interactions.

Designer Collagens were functionalized with photo-crosslinking sites to enable incorporation into a three dimensional hydrogel matrix. Bioactive hydrogels were then fabricated by combining the functionalized Designer Collagens with PEGDA and photocrosslinking via exposure to UV light. The P163 protein forms a stable triple helix similar to native collagen but lacks collagen's intrinsic cell-binding sites. As demonstrated herein, endothelial cells and smooth muscle cells are unable to significantly adhere to P163 containing hydrogels. Thus, the P163 protein provided a blank slate into which binding motifs specific to $\alpha$1$\beta$1 and $\alpha$2$\beta$1 integrins could be inserted in a controlled manner while maintaining the triple helical structure of native collagen. Characterization studies confirmed that the functionalization of Designer Collagens did not disrupt triple helix conformation, integrin binding, or cell adhesion. Initial cell studies also confirmed differential endothelial cell and smooth muscle cell adhesion to GFPGER and GFPGEN-based hydrogels due to selective integrin binding. In particular, the GFPGEN based hydrogels were found to selectively promote adhesion of endothelial cells but not of smooth muscle cells. Since Designer Collagens are non-thrombogenic in terms of platelet aggregation, the spatial localization of various modified Designer Collagens within tissue engineered vascular graft scaffolds may prove to be a powerful tool for promoting luminal endothelial cell adhesion while inhibiting thrombosis and intimal hyperplasia.

The present invention describes the development of semi-synthetic hydrogels that contain Designer Collagens having tunable mechanical properties and controllable bioactivity. Bacterial expression of recombinant Designer Collagens enables a level of batch consistency and economies of scale not possible with solid phase synthesis or native collagen extraction. Conjugation of the Designer Collagens within a synthetic PEG network permits the impact of Designer Collagens on cell behavior to be explored within a mechanically stable hydrogel network and broadens the range of mechanical properties available in the hydrogel design. The present invention describes the use of Designer Collagen Hydrogels (DCH) with properties that recruit selective cell adherence and spreading dependent on the integrin-binding motif included in the Designer Collagen. Cell selectivity is therefore based on the cell's collagen-binding integrin profile. Designer Collagen Hydrogel-1 (or referred to as P163-F) does not contain an integrin binding motif and therefore, does not support optimal adherence or spreading. Designer Collagen Hydrogels-2 (or referred to as GFPGER-based hydrogels) contains $\alpha$11 and $\alpha$12 binding sites. Because of the widespread expression profiles of the collagen-binding integrins, Designer Collagen Hydrogel-2 is an optimal biomaterial for the adherence of many cell types. Designer Collagen Hydrogel-3 (or referred to as GFPGEN-based hydrogels) contains GFPGEN, which selectively binds $\alpha$1, but not $\alpha$2.

Representative uses of Designer Collagen Hydrogels include but are not limited to 1) vascular applications, 2) hernia repair, 3) adhesion prevention, 4) wound healing, and 5) cell delivery. Generally, vascular products include grafts, patches, shunts, catheters and stents. Study of Designer Collagen in combination with hydrogels has resulted in a platform of formulations that direct endothelial cell adhesion and growth while minimizing the potential for thrombosis, intimal hyperplasia, and mechanical failure. Accordingly, the present invention contemplates that Designer Collagen hydrogels may be usefully incorporated into, for example, 1) vascular patches for carotid endarterectomy, dialysis access, bypass functions, and aneurysm treatment; 2) vascular grafts for bypass functions and dialysis access; 3) vascular stenting such as angioplasty or carotid stenting for the treatment of aneurysms, weak vascular, and flow blockage, shunts, which are used in a variety of situations to reroute blood flow; and 4) vascular catheters, for venous access in patients.

Abdominal wall defects may require surgical repair surgery using the tissue or in combination with a medical device, such as mesh. Current mesh-type products, including both synthetic and biological, could be coated with Designer Collagen hydrogels which would provide the cell-material interface. The Designer Collagen hydrogel mesh would be designed to have specific cell-interacting areas and areas that minimize cell-interactions.

Adhesions are scar-like tissues that form between peritoneum surfaces when the normal mesothelial cell layer is perturbed. Efforts to prevent adhesion formation post-surgery are based on barriers or pharmaceuticals. Barrier efforts have resulted in mesh-types and gel-types. Cell types that have been implicated in adhesion formation include myofibroblasts, endothelial cells, and inflammatory cells with wound healing functions. Designer Collagen hydrogels with decreased modulus would function as a gel and be appropriate for laparoscopy procedures. Designer Collagen hydrogels would contain P163, which does not contain any ligand binding sites and therefore, would not allow cell recruitment to the area. The application of Designer Collagen hydrogels to the damaged area would act as a barrier in the colonization of cells that may facilitate adhesion formation.

Wound Healing Applications May Include Chronic or Acute Wounds or Superficial Wounds Adult mesenchymal stem cells (MSCs) are being investigated for their use in regenerative medicine as these cells have the capacity to differentiate into: osteogenic, chondrogenic, adipogenic, myogenic, and neurogenic lineages. Efforts to utilize mesenchymal stem cells in localized areas for tissue growth have met challenges, such as cell retention. Cell retention must be achieved without alteration of the mesenchymal stem cell phenotype, allowing the influx of host factors to the mesenchymal stem cells, and by the support structure being tolerated by existing host tissues. Designer Collagen hydrogels can interact with collagen-binding integrins on the mesenchymal stem cell surface and would therefore function as an optimal cell retention material. Also, directing mesenchymal stem cells towards a specific phenotype has proved challenging. Designer Collagen hydrogels can be used to induce specific cell differentiation by altering the Designer Collagen content and also the properties of the hydrogel itself. Designer Collagens also are a substrate for the adherence of adipocyte stem cells.

The protein, DC3 (containing integrin binding sequence, GFPGEN), possesses a unique characteristic in that it binds α1β1 integrin on the cell surface, but not α2β2. This specific protein-integrin interaction is what determines cell binding specificity, i.e., endothelial adhesion and spreading with minimal smooth muscle cell spreading and a lack of thrombosis. This property gives Designer Collagen hydrogels-3 an advantage in vascular device applications. The protein, DC2 (containing integrin binding sequence, GFPGER), possesses the ability to act as a support for a wide variety of cell types. This characteristic is important when anastomosis of tissue with a device is warranted. An example of this is hernia mesh. DC2 or Designer Collagen hydrogel-2 coated on a mesh would allow for cell adherence and in growth on and around the mesh, and the mesh would contribute support in terms of strength and suture capability.

DC1(P163) is a triple helical protein that does not support the adherence of any cell type tested. This is advantageous because a triple helical protein is resistant to many proteases, thereby, remaining in the body for a longer period of time. This would be appropriate for adhesion prevention therapies. A gel-like substance of DC1 or DCH-1 would not allow the adherence of cells that would eventually lay down fibrotic material.

Hydrogels with Encapsulated MSCs Remain Viable

Figure 18:
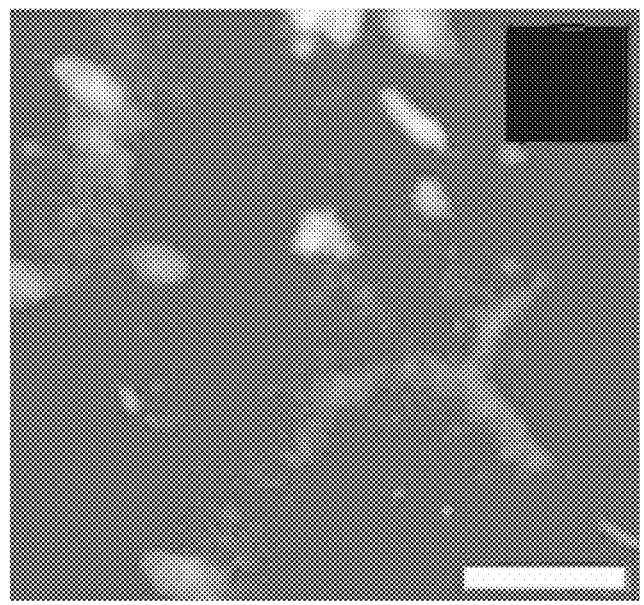
FIG. 18 shows that Designer Collagen Hydrogels with encapsulated MSCs remain viable. Mesenchymal stem cells were mixed with the PEG-DA (3400 g/mol) dissolved in buffer (10 wt %), a photoinitiator (Irgacure 2959) and 1 mg/mL of AC-PEG-DC2 (also referred to as GFPGER-F). The solution was then crosslinked via 90 s exposure to 365 nm UV light (UV-Transilluminator, 9 mW/cm2) and viability assessed after 24 h using a standard Live-Dead kit. MSCs encapsulated within the gel network rapidly spread within the matrix.
Figure 19:
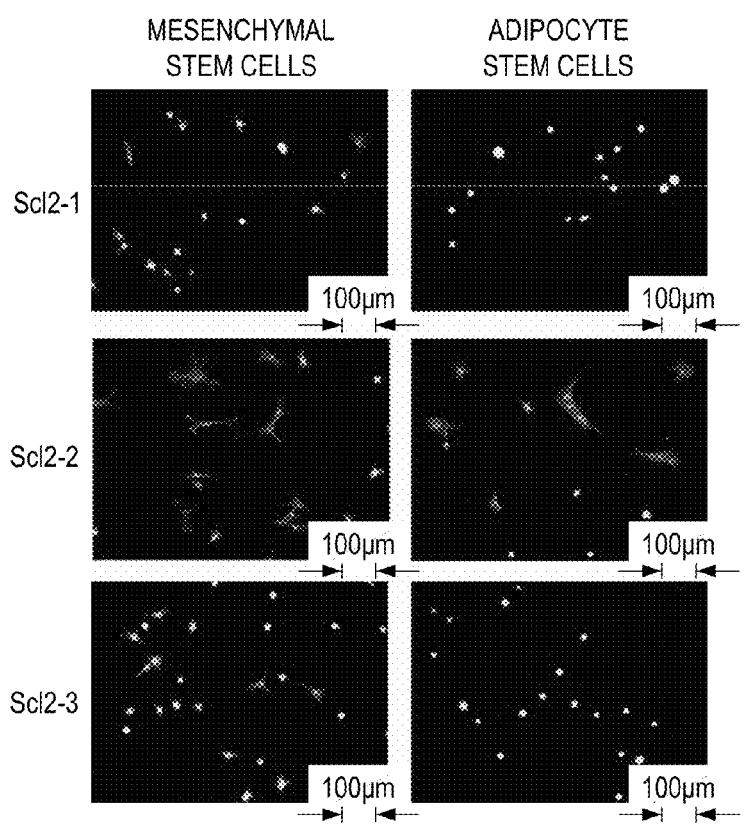
FIG. 19 shows high binding polystyrene 96-well plates coated with P163 (Scl2-1), GFPGER (Scl2-2), and GFPGEN (Scl2-3) at 1 μg protein per well. Mesenchymal stem cells and adipocyte derived stem cells were seeded and allowed to adhere for 3 hours. Attached cells were fixed with 4% paraformaldehyde, stained with rhodamine phalloidin and SybrGreen, and imaged by fluorescence microscopy.

To ensure that cells remained viable while encapsulated in DC hydrogels, mesenchymal stem cells were mixed with the PEG-DA dissolved in buffer, a photoinitiator and AC-PEG-DC2. The solution was then crosslinked via exposure to UV light and viability assessed. MSCs encapsulated within the gel network rapidly spread within the matrix. In addition, Live-Dead staining of mesenchymal stem cells (MSC) encapsulated in PEG-Designer Collagen gels indicated that these gels and the associated polymerization process are cytocompatible (FIG. 18). FIG. 19 shows that both MSC and adipocyte stem cells can adhere and spread on GFPGER, but that MSC adhere and spread on both GFPGER and GFPGEN.

The following references were cited herein:

Xu et al. J Biol Chem 2000 Dec. 15; 275(50):38981-38989.
Kim et al. J Biol Chem 2005 Sep. 16; 280(37):32512-32520.
Xu Y, J Biol Chem 2002 Jul. 26; 277(30):27312-27318.
Humtsoe et al. J Biol Chem 2005 Apr. 8; 280(14):13848-13857.
Sweeney et al. J Biol Chem 2003 Aug. 15; 278(33):30516-30524.
Han et al. Appl Microbiol Biotechnol. 2006 Mar. 22:(72)109-115.
Mohs et al. J Biol Chem 2007 Oct. 12:282(41)29757-29765.
Hoe et al. FEMS Microbiology 2007 Oct. 24:(277)142-149.
Yoshizumi, et al. Protein Sci. 2009 June; 18(6):1241-51.
Caswell, et al. J Biol Chem. 2008 Dec. 26; 283(52):36168-75.

Any patents or publications mentioned in this specification are indicative of the levels of those skilled in the art to which the invention pertains. Further, these patents and publications are incorporated by reference herein to the same extent as if each individual publication was specifically and individually incorporated by reference. One skilled, in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

What is claimed is:

1. A recombinant synthetic collagen comprising an isolated and purified protein produced in a prokaryotic expression system, wherein said protein comprises a collagen-like repeat GXYGX$_1$Y$_2$GX$_2$Y$_2$GXY SEQ ID NO: 13), wherein the amino acid in the X1 position is changed to L, R, or F, and/or the amino acid in the Y2 position is changed to R, K, or N, wherein the recombinant synthetic collagen forms a triple helical backbone.

2. The recombinant synthetic collagen of claim 1, wherein said protein is derived from a Streptococcal protein.

3. The recombinant synthetic collagen of claim 1, wherein said collagen is capable of binding to integrins α1β1 and α2β1 without hydroxyproline.

4. The recombinant synthetic collagen of claim 1, wherein said biologically active sequences are shown in SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, or SEQ ID NO: 12.

5. The recombinant synthetic collagen of claim 4, wherein said collagen containing sequences shown in SEQ ID NO: 4, SEQ ID NO: 7 or SEQ ID NO: 10 support adherence of both α1β1 and α2β1 spreading of endothelial cells, fibroblasts, chondrocytes, and smooth muscle cells.

6. The recombinant synthetic collagen of claim 4, wherein said collagen containing the sequence shown in SEQ ID NO: 11 selectively bind to integrin α1β1, but not to α2β1.

7. The recombinant synthetic collagen of claim 6, wherein said collagen supports adherence of endothelial cells, fibroblasts, and chondrocytic cells, but does not support adherence of smooth muscle cells.

8. The recombinant synthetic collagen of claim 4, wherein said collagen containing the sequence shown in SEQ ID NO: 10 supports adherence and spread of mesenchymal stem cells or adipocyte stem cells.

9. The recombinant synthetic collagen of claim 4, wherein said collagen containing the sequence shown in SEQ ID NO: 11 supports adherence and spread of mesenchymal stem cells.

10. The recombinant synthetic collagen of claim 4, wherein said collagen containing sequences shown in SEQ ID NO: 4, SEQ ID NO: 7, SEQ ID NO: 10, or SEQ ID NO: 11 do not aggregate platelets and are non-thrombogenic.

11. The recombinant synthetic collagen of claim 4, wherein said collagen containing a GFPGER (SEQ ID NO: 10) sequence inhibits collagen-induced platelet aggregation.

12. The recombinant synthetic collagen of claim 4, wherein said collagen containing the sequence shown in SEQ ID NO: 11 does not inhibit collagen-induced platelet aggregation.

13. The recombinant synthetic collagen of claim 4, wherein said collagen contains one, two, three, four or five multiple cell binding motifs results in a density dependent increase in integrin affinity, cell binding, and cell migration.

14. The recombinant synthetic collagen of claim 13, wherein said collagen contains one, two, three, four or five cell binding motifs shown in SEQ ID NO: 4.

15. The recombinant synthetic collagen of claim 1, wherein said collagen is affixed to or linked in a chemical manner to a scaffold with intrinsic tensile properties.

16. The recombinant synthetic collagen of claim 15, wherein said scaffold is selected from the group consisting of PEG-containing hydrogels, ECM components, and mesh materials.

17. The recombinant synthetic collagen of claim 1, further comprising an insert selected from the group consisting of bone sialoprotein binding sequences, integrins a α10β1 and α11β1 binding sequences, and an extracellular matrix constituent.

18. The recombinant synthetic collagen of claim 1, wherein said collagen is produced in a prokaryotic expression system deficient in post-translational modification.

* * * * *